US012622971B2

(12) United States Patent
Myers et al.

(10) Patent No.: US 12,622,971 B2
(45) Date of Patent: May 12, 2026

(54) LINEAR POLYSACCHARIDE BASED FILM PRODUCTS

(71) Applicant: Aquestive Therapeutics, Inc., Warren, NJ (US)

(72) Inventors: Garry L. Myers, Kingsport, TN (US); Michael Li, Warren, NJ (US); Beuford Arlie Bogue, Warren, NJ (US); Eric Dadey, Sevierville, TN (US)

(73) Assignee: Aquestive Therapeutics, Inc., Warren, NJ (US)

( * ) Notice: Subject to any disclaimer, the term of this patent is extended or adjusted under 35 U.S.C. 154(b) by 160 days.

(21) Appl. No.: 17/489,128

(22) Filed: Sep. 29, 2021

(65) Prior Publication Data

US 2022/0088201 A1 Mar. 24, 2022

Related U.S. Application Data

(63) Continuation of application No. 16/830,448, filed on Mar. 26, 2020, now abandoned, which is a continuation of application No. 16/002,643, filed on Jun. 7, 2018, now abandoned, which is a continuation of application No. 15/534,630, filed as application No. PCT/US2015/064806 on Dec. 9, 2015, now abandoned.

(60) Provisional application No. 62/089,676, filed on Dec. 9, 2014.

(51) Int. Cl.
| | |
|---|---|
| *A61K 47/36* | (2006.01) |
| *A61K 9/00* | (2006.01) |
| *A61K 31/4545* | (2006.01) |
| *A61K 31/4985* | (2006.01) |
| *A61K 31/519* | (2006.01) |
| *C08B 37/00* | (2006.01) |
| *A61K 31/197* | (2006.01) |
| *A61K 31/404* | (2006.01) |

(52) U.S. Cl.
CPC .............. *A61K 47/36* (2013.01); *A61K 9/006* (2013.01); *A61K 31/4545* (2013.01); *A61K 31/4985* (2013.01); *C08B 37/0018* (2013.01); *A61K 31/197* (2013.01); *A61K 31/404* (2013.01); *A61K 31/519* (2013.01)

(58) Field of Classification Search
CPC .... A61K 47/36; A61K 9/006; A61K 31/4545; A61K 31/4985; A61K 31/197; A61K 9/7007; A61K 9/7015; A61K 47/26; C08B 37/0018; A61P 9/12; A61P 1/12; A61P 11/14; A61P 15/10; A61P 23/00; A61P 25/00; A61P 25/04; A61P 25/18; A61P 25/20; A61P 29/00; A61P 31/04
See application file for complete search history.

(56) References Cited

U.S. PATENT DOCUMENTS

| | | | | |
|---|---|---|---|---|
| 5,948,430 | A * | 9/1999 | Zerbe ...................... | A61P 11/00 424/435 |
| 2006/0198873 | A1 | 9/2006 | Chan et al. | |
| 2006/0204559 | A1* | 9/2006 | Bess .................... | A61K 9/7007 424/443 |
| 2008/0057087 | A1 | 3/2008 | Krumme | |
| 2008/0233174 | A1* | 9/2008 | Myers .................... | A61K 9/006 424/435 |
| 2010/0215774 | A1 | 8/2010 | Maibach | |
| 2013/0005831 | A1* | 1/2013 | Rajewski ............. | A61K 9/0056 514/777 |
| 2015/0025084 | A1 | 1/2015 | Jeong et al. | |

FOREIGN PATENT DOCUMENTS

| | | | | | |
|---|---|---|---|---|---|
| CA | 2864322 | A1 * | 9/2013 | ........... | A61K 31/519 |
| CN | 1829490 | A | 9/2006 | | |
| WO | 0170194 | A1 | 9/2001 | | |
| WO | 2005004989 | A2 | 1/2005 | | |
| WO | WO-2010146601 | A1 * | 12/2010 | ............. | A61K 31/00 |
| WO | WO-2012053006 | A2 * | 4/2012 | ............. | A61K 47/38 |
| WO | 2013/085224 | A1 | 6/2013 | | |
| WO | 2016/094567 | A1 | 6/2016 | | |

OTHER PUBLICATIONS

Wu et al, Non-traditional plasticization of polymeric films, International Journal of Pharmaceutics 177 (1999), 15-27. (Year: 1999).*
International Search Report dated Mar. 9, 2016 issued in PCT/US2015/064806 (3 pages).
Written Opinion of the International Searching Authority dated Mar. 9, 2016 issued in PCT/US2015/064806 (5 pages).
International Preliminary Report on Patentability dated Jun. 13, 2017 issued in PCT/US2015/064806 (6 pages).

* cited by examiner

*Primary Examiner* — Mina Haghighatian
(74) *Attorney, Agent, or Firm* — Hoffmann & Baron, LLP

(57) ABSTRACT

Film products, especially suitable for oral delivery, which can be formed during manufacture in the form of large and/or heavy film strips or sheets and subsequently cut into uniform dosage units, each dosage unit being uniform in content and having distributed therein a linear polysaccharide, such as pullulan, a plasticizer, and an active component.

16 Claims, 13 Drawing Sheets

Polymer Type PID Comparison

Examples 23-32

Examples 23-32

Pharmacokinetic Profile of Sildenafil Citrate™ 50 mg
PharmFilm in Beagle Dogs Following Oral Administration Pharmacokinetic Profile of Viagra™ 50 mg Tablet
in Beagle Dogs Following Oral Administration Apr. 2013

Pharmacokinetic Profile of Sildenafil Citrate 50 mg
PharmFilm™
in Beagle Dogs Following Oral Administration Pharmacokinetic Profile of Sildenafil 50 mg PharmFilm™ (in capsule) in Beagle Dogs Following Oral Administration Apr. 2013

Pharmacokinetic Profile of Sildenafil Resinate 50 mg PharmaFilm™ in Beagle Dogs Following Oral Administration

LINEAR POLYSACCHARIDE BASED FILM PRODUCTS

CROSS-REFERENCE TO RELATED APPLICATIONS

This application is a continuation of U.S. application Ser. No. 16/830,448, filed Mar. 26, 2020, which is a continuation of U.S. application Ser. No. 16/002,643, filed Jun. 7, 2018, which is a continuation of U.S. application Ser. No. 15/534, 630, filed Jun. 9, 2017, which is a National Stage of International Application No. PCT/US2015/064806, filed Dec. 9, 2015, which claims the benefit of U.S. Provisional Application No. 62/089,676, filed Dec. 9, 2014; the entire contents of each of the foregoing applications is incorporated by reference herein.

FIELD OF THE INVENTION

The invention relates to pharmaceutical film products, especially suitable for oral delivery, which can be formed during manufacture in the form of large and/or heavy film strips or sheets and subsequently cut into uniform dosage units, each dosage unit being uniform in active content and having distributed therein a linear polysaccharide as the polymer platform, such as pullulan, a plasticizer, other film forming excipients, and an active component.

BACKGROUND OF RELATED TECHNOLOGY

Pullulan is a relatively high molecular weight polymer yet has low viscosity and high solids loading due to its high water solubility. For example, a 10% solids solution of pullulan with an average molecular weight of 200,000 Daltons in 30° C. water has a viscosity of 130-180 centipoise. Films made with Pullulan tend to dissolve quickly. However, Pullulan also has some negative properties when it is manufactured on high speed mixing equipment. Used alone, it is brittle and shock sensitive and if plasticized, it is difficult to incorporate sufficient plasticizer into the formulation to decrease or eliminate shock sensitivity without the film becoming tacky. To get around these adverse properties, water is often used as a plasticizer with and without starch, xanthan and gellan gum. The films are dried with relatively high amounts of moisture left in the film, as much as 5-10%. However, high moisture content can increase the water activity of the film strips and thus become a breeding ground for microbial growth. Also, water (moisture content) tends to evaporate from such formulations over time and the loss of the plasticizer (water) leads to brittleness of the finished film as the film ages.

Low tackiness, lack of shock sensitivity and lack of brittleness are all important physical attributes of a robust "production quality" polymer formulation for oral soluble films. The manufactured oral soluble film web undergoes many unit operations during the drying, slitting, storing and packaging production steps. Film webs with improper adhesion or release characteristics can result in jamming of the packaging line which brings the manufacturing process to a halt. The same jamming occurs with any film web that is brittle. Shock sensitivity is also important attribute of the film web, especially during the film slitting process, as a shock sensitive film web will experience crazing, and shatter like a broken glass, rather than propagating the failure in the direction of the knife, which results in a clean and even cut like paper. This leads to unusable product and a stalled low-yield manufacturing process.

Self-supporting linear polysaccharide (e.g., glucan) films, such as those made from pullulan and elsinan, are known as being useful for the delivery of edible or ingestible components (e.g., commercial breath films), for packaging and wrapping as well as other uses. For example, U.S. Pat. No. 4,562,020 to Haijiya, et al. discloses a continuous process for producing such self-supporting glucan films formed from aqueous glucan solutions whereby the solution is deposited on a corona-treated plastic conveyor belt and air dried to form films.

U.S. Pat. No. 4,927,636 to Haijiya, et al. discloses pullulan films which have decreased solubility in water. These films are made from a combination of pullulan and polyethylene glycol (PEG) which form an "association complex" to produce this effect. Polyethylene glycols within the molecular weight range of 400 to 10,000 Daltons are disclosed as useful. The ratio of pullulan to PEG is disclosed as being 1 part by weight (pbw) pullulan to 0.01 to 100 part by weight (pbw) PEG. This patent discloses that pullulan in combination with other water-soluble polymers does not form such an association complex useful for decreasing solubility and reducing adhesive and stickiness properties of aqueous pullulan.

U.S. Pat. No. 5,411,945 to Ozaki, et al. discloses a pullulan binder composition made from a combination of pullulan and a mono-saccharide or lower molecular weight oligo-saccharide in a ratio of 85:15 to 65:35 pullulan/saccharide. These films are disclosed as being gradually dissolvable.

U.S. Pat. No. 5,518,902 to Ozaki, et al. discloses high pullulan content products made by cultivating micro-organisms capable of producing pullulan at a pH exceeding 2.0 but not higher than 4.0 in a nutrient culture medium containing 10-20 w/v % of a polysaccharide to produce pullulan, while controlling the viscosity of the nutrient culture to below 30 cps.

U.S. Patent Application Publication No. 2001/0022964 A1 to Leung, et al. discloses edible films made from pullulan and which include anti-microbial effective amounts of essential oils.

While various active pharmaceutical ingredients may be included in the films, the content of pullulan used is very high and the drug loading is very low, as is typical of pullulan films. In addition, a variety of polymers may be used as film formers in addition to pullulan.

It would be desirable to have film products made from pullulan which can include high content of active pharmaceutical ingredients, such as pharmaceutical and/or cosmetic agents, and which have relatively low pullulan content. It would also be desirable to manufacture "production quality" film products containing pullulan that are robust enough to withstand high speed production and packaging unit operations and that will stay flexible over time after the packaging operation. It would also be advantageous to provide water-soluble and/or dispersible, edible films which have a uniformity of active pharmaceutical ingredient content, both at production scale and in the packaged unit, whereby the active content of the final unit dose film product varies by no more than 10% from the desired level of active pharmaceutical ingredient.

SUMMARY OF THE INVENTION

The present invention seeks to attain low polymer content, high pharmaceutical and/or cosmetic active content orally dissolvable films which have enhanced flexibility, structural integrity, uniformity, and possess disintegration and/or dissolution times of less than 5 minutes when placed into contact with any of several body surfaces, especially those including mucosal surfaces, such as those found in the oral (i.e., sublingual, lingual, buccal, and gingival), anal, vaginal, ocular, nasal, aural, ophthalmological, and peritoneal environments; the surface of a wound, either on a skin surface or within the body such as during surgery or left in place after surgery to deliver the desired amount of active after the surgical procedure is completed; the surface of an organ (i.e., kidney, lung, liver, heart, etc.), and other similar surfaces. In certain instances, in the film products of the invention four to five times more film weight can be loaded into the same size film (area) and while maintaining a similar Partial Immersion Dissolution (PID) time when compared to traditional polymer film formulations.

In an embodiment, the films of the invention have a disintegration and/or dissolution time that is less than about 4 minutes, less than about 3 minutes, less than about 2 minutes, less than about 1.5 minutes, less than 1 minute, less than about 45 seconds, less than about 30 seconds, less than about 20 seconds, less than about 15 seconds, less than about 10 seconds, or less than about 5 seconds. In embodiments, the disintegration and/or dissolution time is in the range of from about 5 seconds to about 5 minutes, from about 10 second to about 4 minutes, from about 15 seconds to about 2 minutes, from about 20 seconds to about 1.5 minutes, from about 30 second to about 90 seconds, or about 5 seconds to about 1 minute.

In one embodiment of the present invention, there is provided a film product including: a. at least one linear polysaccharide; b. a therapeutically effective amount of at least one active component; and c. at least one plasticizer.

In a further embodiment of the present invention, there is provided a film product including: a. pullulan; b. a therapeutically effective amount of sildenafil or a pharmaceutically acceptable salt thereof; and c. at least one plasticizer.

In one embodiment of the present invention, there is provided a film product including: a. pullulan; b. a therapeutically effective amount of a pregabalin; and c. at least one plasticizer.

In one embodiment of the present invention, there is provided a film product including: a. pullulan; b. a therapeutically effective amount of tadalafil; and c. at least one plasticizer.

DETAILED DESCRIPTION OF THE INVENTION

Figure 1:
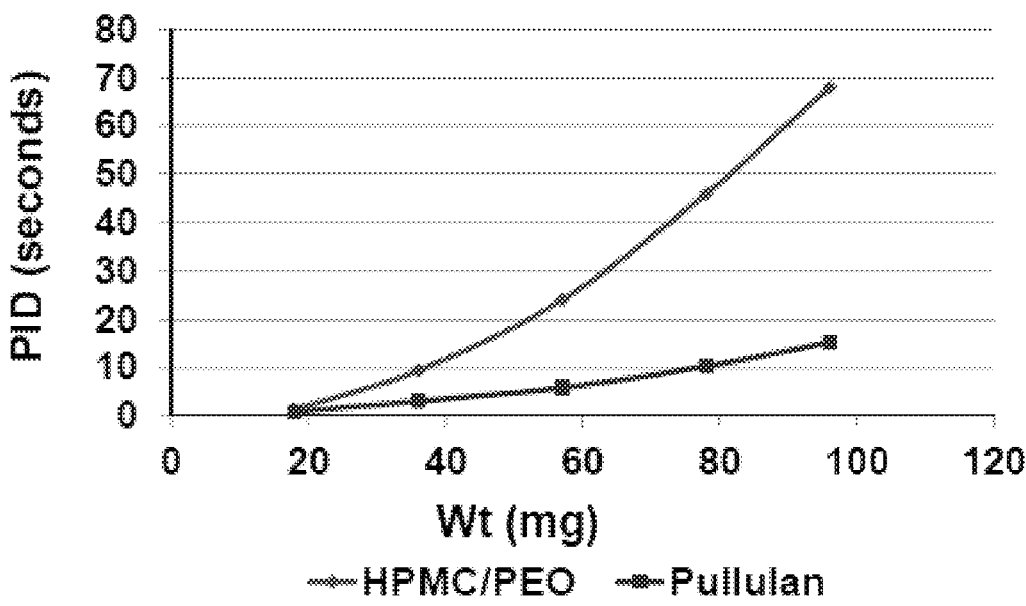
FIG. 1 shows a comparison of the partial immersion dissolution time for the comparative film compositions (HPMC/PEO) and inventive film products (Pullulan).

The term "linear polysaccharide" means polymeric compounds including long chains of monosaccharides bound to one another through glycosidic bonds and having a substantially linear structure. As used herein "polysaccharide" may include any molecule including more than 2 monosaccharides bound together. In aspects of the invention, the linear polysaccharide is a polysaccharide with an alpha 1,4 or an alpha 1,6 glycosidic linkage.

Preferably the linear polysaccharides of the invention have low glass transition temperatures (less than room temperature). For example, glass transition temperatures for pullulan, dextrose, and amylose are −73° C., −94° C., and −59° C. respectively. In particular, preferred polysaccharides of the invention have β(1-4 glycosidic bonds) and α(1-4 glycosidic bonds), which offer exceptional rotational freedom. β(1-4 glycosidic bonds) are favored in linear or stretched chain conformations and are favorable because they resist the helical conformation associated with α(1-4 glycosidic bonds) and the semicrystalline structure that accompanies it. In either case, the low glass transition temperature affords sufficient free volume for highly loaded films, while affording the mechanical integrity for a flexible, manufacturable film.

Linear polysaccharides for use in the present invention include glucans. As used herein, "Glucan" means a polysaccharide of D-glucose monosaccharides bound to one another through glycosidic bonds.

Glucans useful in the present invention include pullulan and elsinan. These materials substantially contain repeating maltotriose units and are produced by culturing a strain of species *Aureobasidium pullulans* or genus Elsino on a nutrient medium containing sugars under aeration and agitation conditions. The cellular debris is removed and the resultant supernatant is purified and filtered to yield the resultant glucan. The molecular weight of the glucan may vary widely, but generally are commercially available in grades that are designated as having molecular weights of about 8,000 to greater than 2,000,000 Daltons. Preferably, the glucan of the present invention is designated as having a molecular weight between about 25,000 and about 500,000 Daltons, more preferably, between about 50,000 to about 200,000 Daltons. It is well understood that these grades are blends of molecular weights and not absolute values.

In aspects of the invention, the linear polysaccharide is maltose 1,4; raffinose 1-6; meibiose 1,6; laltotriose 1,4; maltotriose 1,4; maltotetralose 1,4; maltopentalose 1,4; linear dextrins 1,4; linear dextrins 1,6; or combinations thereof.

The linear polysaccharide may be present in amounts up to about 75% by weight of the total composition and desirably in amounts of up to about 40% by weight of the total composition. In aspects of the invention the linear polysaccharide may be present in amounts of about 10% to about 35% by weight of the total composition. In other aspects of the invention the linear polysaccharide may be present in amounts of about 15% to about 25% by weight of the total composition. In an aspect of the invention the linear polysaccharide may be present in an amount of about 18% of the total composition.

The film product of the invention may further include an additional film-forming polymer. The additional film-forming polymer or polymers may be a water soluble, water swellable, water miscible, water dispersible, or a combination of one or more either water soluble, water swellable, water miscible, or water dispersible polymers. The additional film-forming polymer may include cellulose or a cellulose derivative. Specific examples of useful water soluble polymers include, but are not limited to, polyethylene oxide (PEO), hydroxypropylmethyl cellulose (HPMC), hydroxyethyl cellulose, hydroxypropyl cellulose (HPC), polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water miscible polymers or water dispersible polymers include, but are not limited to, ethyl cellulose, hydroxypropyl ethyl cellulose, cellulose acetate phthalate, hydroxypropyl methyl cellulose phthalate, hydroxypropylmethylcellulose acetate succinate ("HPMCA"), and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being "water swellable polymers." The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other additional film-forming polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid)(PLA), polydioxanones, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly (lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific additional film-forming polymers useful include those marketed under the Medisorb and Biodel trademarks. The Medisorb materials are marketed by the Dupont Company of Wilmington, Delaware and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°–347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50/lactide and 50% glycolide with a melting point within the range of 338°-347° F. (170°-175° C.). Lactide/glycolide copolymers with other ratios of lactide to glycolide are also useful additional film-forming polymers.

The Biodel materials represent a family of various polyanhydrides which differ chemically.

In aspects of the invention the additional film-forming polymer is a natural polymer.

In aspects of the invention the additional film-forming polymer is hydroxypropylmethylcellulose acetate succinate ("HPMCA").

Preferred examples of useful additional film-forming polymers include hydroxypropylmethyl cellulose, hydroxyethyl cellulose, hydroxypropyl cellulose, carboxymethyl cellulose, ethyl cellulose, hydroxypropyl ethyl cellulose, cellulose acetate phthalate, hydroxypropyl methyl cellulose phthalate, sodium alginate, polyethylene glycol, xanthan gum, tragancanth gum, locust bean gum, pea starch, carrageenan, taro root gum, guar gum, acacia gum, arabic gum, starch, gelatin, and combinations thereof.

The film products of the invention will have a total polymer content that includes the linear polysaccharide and any additional film-forming polymer, if present.

The film product of the present invention further includes an active component selected from pharmaceutical agents, medicaments, drugs, bioactive agents, cosmetic agents, and combinations thereof. The active component may be present in any desired amount effective for the intended treatment. It is particularly desirable and an advantage of the present invention that the active component can be included at high loading. For example, the active component may be present in amounts up to about 65% by weight of the total composition. In aspects of the invention the active component is present in amounts of about 40% or greater, 45% or greater, 50% or greater, or 55% or greater, or 60% or greater by weight of the total composition. In other aspects the active component is present in an amount of about 0.01% to about 60% by weight of total composition.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulants, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Erectile dysfunction therapies include, but are not limited to, drugs for facilitating blood flow to the penis, and for effecting autonomic nervous activities, such as increasing parasympathetic (cholinergic) and decreasing sympathetic (adrenergic) activities. Useful non-limiting oral phosphodiesterase Type V (PDE5) inhibitor drugs include sildenafils, such as Viagra®, tadalafils, such as Cialis®, vardenafils such as Lavitra®, apomorphines, such as Uprima®, yohimbine hydrochlorides such as Aphrodyne®, alprostadils such as Caverject®, phentolamines, udenafil, and avanafil. Other useful drugs work by increasing the nitric oxide production such as arginine, PNTX2-6 (Phoneutria nigrivente-spider toxin) and forskolin and serotonin agonists like trazodone. Other useful compounds include those that work to relax the corporal smooth muscle tissue by inhibition of neutral endopeptidase, such as sialorphin, which is an opiorphin. Also useful in the present invention is the buccal absorption of stem cells. The use of gene therapy agents are also envisioned as a possible therapy for use in the present invention.

Among the useful sildenafils are sildenafil citrate, sildenafil hydrochloride, sildenafil resinate, sildenafil hydrogensulphate, sildenafil hemisulphate, sildenafil hemitartrate, sildenafil esylate, sildenafil fumarate, sildenafil lactate, sildenafil base, and combinations thereof. A preferred sildenafil is sildenafil citrate.

When present the sildenafil may be included in an amount of about 10% to about 65% by weight based on the total weight of the film product. In aspects of the invention, a sildenafil may be present in amounts of about 20% to about 65% based on the total weight of the film product. In aspects of the invention, a sildenafil may be present in amounts of about 40% to about 65% based on the total weight of the film product. In other aspects of the invention, a sildenafil may be present in amounts of about 60% to about 65% based on the total weight of the film product.

In other aspects of the invention the film product is a dosage unit and the sildenafil is present in the dosage unit in an amount equivalent to about 5 to about 200 milligrams of sildenafil base; for example in an amount equivalent to about 25 to about 100 milligrams of sildenafil base. In other aspects of the present invention, the film product is a dosage unit and the sildenafil is present in the dosage unit in an amount equivalent to about 25, about 50, about 70, or about 100 milligrams of sildenafil base.

In other aspects of the invention the film product active component is a pregabalin. Among the useful pregabalins are pregabalin acid, pregabalin hydrochloride, pregabalin hydrobromides, pregabalin hydrosulfate, pregabalin mandelate, pregabalin besylate, pregabalin tosylate, and combinations thereof. A preferred pregabalin is pregabalin acid.

When present the pregabalin may be included in an amount of about 40% to about 80% by weight based on the total weight of the film product. In aspects of the invention, a pregabalin may be present in amounts of about 60% to about 75% based on the total weight of the film product. In aspects of the invention, a pregabalin may be present in amounts of about 65% to about 75% based on the total weight of the film product.

In other aspects of the invention the film product is a dosage unit and the pregabalin is present in the dosage unit in an amount equivalent to about 5 to about 300 milligrams of pregabalin acid; for example in an amount equivalent to about 25 to about 150 milligrams of pregabalin acid. In other aspects of the present invention, the film product is a dosage unit and the pregabalin is present in the dosage unit in an amount equivalent to about 150 milligrams of pregabalin acid.

In other aspects of the invention the film product active component is a tadalafil. When present the tadalafil may be included in an amount of about 5% to about 65% by weight based on the total weight of the film product. In aspects of the invention, a tadalafil may be present in amounts of about 10% to about 65% based on the total weight of the film product. In aspects of the invention, a tadalafil may be present in amounts of about 20% to about 65% based on the total weight of the film product. In aspects of the invention, a tadalafil may be present in amounts of about 5% to about 20% based on the total weight of the film product. In other aspects of the invention, a tadalafil may be present in amounts of about 60% to about 65% based on the total weight of the film product.

In other aspects of the invention the film product is a dosage unit and the tadalafil is present in the dosage unit in an amount of about 1 to about 100 milligrams; for example in an amount of about 2 to about 50 milligrams, in yet another example from about 5 to about 20 milligrams. In other aspects of the present invention, the film product is a dosage unit and the tadalafil is present in the dosage unit in an amount of about 5, about 10, or about 20 milligrams.

In aspects of the invention, the active component employed in the present invention may be incorporated into the film compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

The active component may be taste-masked prior to incorporation into the film composition, as set forth in the PCT Application No. PCT/US02/32594, entitled Uniform Films For Rapid Dissolve Dosage Form Incorporating Taste-Masking Compositions, based on U.S. Provisional Application No. 60/414,276 of the same title, filed Sep. 27, 2002, the entire subject matter of which is incorporated by reference herein.

Examples of medicating active components contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®, Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), capsaicin (commercially available as Qutenza®), morphine sulfate and naltrexone hydrochloride (commercially available as Embeda®), hydromorphone hydrochloride (commercially available as Dilaudid®), propoxyphene napsylate and acetaminophen (commercially available as Darvocet-N®), Fentanyl (commercially available as Duragesic®, Onsolis®, and Fentora®), sodium hyaluronate (commercially available as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular® or Acuvail®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), diclofenac potassium (commercially available as Cambia® or Zipsor®), and misoprostol (commercially available as Cytotec®). Opiate derivative, including opiate agonists and antagonists, such as buprenorphine and naloxone are further examples of drugs for use in the present invention.

Other preferred active ingredients for use in the present invention include anti-diarrheals such as loperamide (commercially available as Imodium AD®, Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners/deodorizers. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethorphan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), bepotastine besilate (commercially available as Bepreve®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenhydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), caprylidene (commercially available as Axona®), and memantine (commercially available as Namenda®); anemia medication, such as cyanocobalamin (commercially available as Nascobal®) and ferumoxytol (commercially available as Feraheme®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifenesin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); angioedema medication, such as C1 esterase Inhibitor (human)(commercially available as Berinert®) and ecallantide (commercially available as Kalbitor®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethyl-succinate/Sulfisoxazole acetyl (commercially available as Pediazole®), and levofloxacin (commercially available as Levaquin®).

The present invention may further include one or more antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), besifloxacin (commercially available as Besivance®), clarithromycin (commercially available as Biaxin®), ceftibuten (commercially available as Cedax®), cefuroxime axetil (commercially available as Ceftin), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), dexamethasone (commercially available as Ozurdex®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), bevacizumab (commercially available as Avastin®), everolimus (commercially available as Afinitor®), pazopanib (commercially available as Votrient®), and anastrozole (commercially available as Arimidex®); leukemia treatment, such as ofatumumab (commercially available as Arzerra®); anti-thrombotic drugs, such as antithrombin recombinant lyophilized powder (commercially available as Atryn®), prasugrel (commercially available as Efient®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), canakinumab (commercially available as Llaris®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®), certolizumab pegol (commercially available as Cimzia®), diclofenac sodium (commercially available as Pennsaid®), golimumab (commercially available as Simponi®), and tocilizumab (commercially available as Actemra®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan® or Gelnique®), darifenacin (commercially available as Enablex®), and solifenacin succinate (commercially available as VESIcare®); blood vessel constrictors, such as methylergonovine maleate (commercially available as Methergine®); plasma uric managers, such as rasburicase (commercially available as Elitek®); iron deficiency anemia medications, such as ferumoxytol (commercially available as Feraheme®); lymphoma medications, such as pralatrexate (commercially available as Folotyn®), romidepsin (commercially available as Isodax®); malaria medication, such as artemether/lumefantrine (commercially available as Coartem®); hyponatremia medication, such as tolvatpan (commercially available as Samsca®); medication for treatment of von Willebrand disease (commercially available as Wilate®); anti-hypertension medications, such as treprostinil (commercially available as Tyvaso®), tadalafil (commercially available as Adcirca®); cholesterol lowering medication, including paricalcitol (commercially available as Altocor®), pitavastatin (commercially available as Livalo®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), bromocriptine mesylate (commercially available as Cycloset®), liraglutide (commercially available as Victoza®), saxagliptin (commercially available as Onglyza®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec), pantoprazole sodium (commercially available as Protonix®), metoclopramide hydrochloride (commercially available as Reglan® or Metozolv®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); fibromyalgia medication, such as milnacipran hydrochloride (commercially available as Savella®); medication for the treatment of gout, such as colchicine (commercially available as Colcrys®), and febuxostat (commercially available as Uloric®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Agents useful herein may further include eye medications and treatment, such as dipivefrin hydrochloride (commercially available as Propine®), valganciclovir (commercially available as Valcyte®), ganciclovir ophthalmic gel (commercially available as Zirgan®); bepotastine besilate (commercially available as Bepreve®), besifloxacin (commercially available as Besivance®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); influenza medication, such as haemophilus b conjugate vaccine; tetanus toxoid conjugate (commercially available as Hiberix®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), Guanabenz acetate. (commercially available as Wytensin®), Guanfacine hydrochloride (commercially available as Tenex® or Intuniv®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®) or human papillomavirus bivalent (commercially available as Cervarix®); immunosuppressants, including cyclosporine (commercially available as Gengraft®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), tranexamic acid (commercially available as Lysteda®), and norethindrone acetate (commercially available as Aygestin®); and muscle relaxants, including cyclobenzaprine hydrochloride (commercially available as Flexeril), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease® or Zenpep®); medication for the treatment of Parkinson's disease, such as pramipexole dihydrochloride (commercially available as Mirapex), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); multiple sclerosis medication, such as dalfampridine (commercially available as Ampyra®) and interferon beta-I b (commercially available as Extavia®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft), asenapine (commercially available as Saphris®), iloperidone (commercially available as Fanapt®), paroxetine hydrochloride (available as Paxil®), aripiprazole (commercially available as Abilify®), guanfacine (commercially available as Intuniv®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid)(commercially available as Depakote®), dextroamphetamine sulfate (commercially available as Dexedrine), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil), protriptyline hydrochloride (commercially available as Vivactil®), bupropion hydrochloride (commercially available as Wellbutrin®, Wellbutrin SR®, and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), vigabatrin (commercially available as Sabril®), and topiramate (commercially available as Topamax®); treatment for shingles, such as zoster vaccine live (commercially available as Zostavax®); skin care medications, including calcipotriene (commercially available as Dovonex®), ustekinumab (commercially available as Stelara®), televancin (commercially available as Vibativ®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solagd®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®), eszopiclone (available as Lunesta®), zolpidem tartrate (commercially available as Ambien®, Ambien CR®, Edluar®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono- or dibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

An anti-oxidant may also be added to the film to prevent the degradation of an active, especially where the active is oxidation sensitive, for example, photosensitive.

Cosmetic active agents may include breath freshening compounds such as d-menthol and l-menthol, other flavors; such as mint, cherry, lemon lime, mixed berry, grapefruit, eucalyptol, methyl salicylate, and thymol, or fragrances, especially those used for oral hygiene, as well as actives used in dental and oral cleansing such as quaternary ammonium bases, hydrogen peroxide, moisturizers, and vitamin E. The effect of flavors may be enhanced using flavor enhancers like tartaric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments include, for example the oxides of iron or titanium. The oxides of iron or titanium are preferably added in concentrations ranging from about 0.001 to about 10%, and more preferably in amounts of about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), sucrose, dextrose, invert sugar, fructose, and combinations thereof; saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, maltitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

Plasticizers useful in the films of the invention include, for example, xylitol, polyalkylene oxides, such as polyethylene glycols, polypropylene glycols, polyethylene-propylene glycols; organic plasticizers with low molecular weights, such as glycerol (glycerin), glycerol monoacetate, diacetate or triacetate, triacetin, polysorbate, cetyl alcohol, propylene glycol, sorbitol, sodium diethylsulfosuccinate, triethyl citrate, tributyl citrate, and the like.

When using linear polysaccharides, such as pullulan, in making oral soluble films there is a fine line between tackiness and brittleness evidenced much more so with Pullulan than with other polymer systems. A narrow selection of plasticizers exists that result in flexible film that is not tacky, brittle, or fracture sensitive. There is also a preferred selection and combination of plasticizers that stand out for producing oral soluble films (OSF) that pass all subjective tests for high speed film production and packaging and storage.

Such combinations of plasticizers may result in the ability to load higher amounts of active pharmaceutical ingredient per film and still allow the films to dissolve at a faster Partial Immersion Dissolution (PID) when compared to a traditional type of OSF polymer formulation. Moreover, among the narrow plasticizer selection there is a preferred range of plasticizer amounts.

Accordingly, the plasticizers useful in the present invention include xylitol, glycerin, and combination thereof. The plasticizer is present in an amount of about 10% to about 45% by weight based on the combined weight of the plasticizer and the total polymer content. In an aspect of the invention the plasticizer is present in an amount of about 10% to about 40% by weight based on the combined weight of the plasticizer and the total polymer content. In another aspect of the invention the plasticizer is present in an amount of about 15% to about 22.5% by weight based on the combined weight of the plasticizer and the total polymer content. In yet another aspect of the invention the plasticizer is present in an amount of about 18% to about 21% by weight based on the combined weight of the plasticizer and the total polymer content.

As discussed above, previous attempts to produce useful pullulan film have used water as a plasticizer with and without starch, xanthan and gellan gum. However, these films are dried with relatively high amounts of water left in the film, as much as 5-10%, which can make them a breeding ground for microbial growth in some situations. Moreover, water (residual moisture in the film) tends to evaporate from such formulations over time and the loss of the plasticizer (water) leads to brittleness of the finished film as the film ages.

In aspects of the invention, the film product is substantially free of water. For example, the water content of the film product of the invention is about 10% or less by weight, preferably about 5% or less by weight of the total weight of the film product. In an aspect of the invention, the water content of the film product is about 4% or less by weight, or about 2% or less by weight, based on the total weight of the film product.

The film product of the invention may further include an acid. In an aspect of the invention the acid is a water soluble carboxylic acid. Examples of useful acids include citric acid, formic acid, acetic acid, propionic acid, ascorbic acid, lactic acid, malic acid, tartaric acid, and combinations thereof. When present in the film product the acid is in an amount of about 0.1% to about 10% by weight based on the total weight of the film product. In an aspect of the invention the acid is present in an amount of about 2 to about 6% by weight, or about 5% by weight, based on the total weight of the film product. In an aspect of the invention the acid is citric acid.

In an aspect of the invention the plasticizer is a xylitol, which is present in an amount of about 10% to about 45% by weight based on the combined weight of the xylitol and the total polymer content. In another aspect of the invention the plasticizer is a xylitol, which is present in an amount of about 20 to about 40% by weight based on the combined weight of the xylitol and the total polymer content.

In an aspect of the invention the plasticizer is a glycerin, which is present in an amount of about 15% to about 22.5% by weight based on the combined weight of the glycerin and the total polymer content. In another aspect of the invention the plasticizer is a glycerin, which is present in an amount of about 18 to about 21% by weight based on the combined weight of the glycerin and the total polymer content.

In an aspect of the invention the plasticizer is a combination of xylitol and glycerin, wherein 1) the amount of glycerin is about equal to or less than the amount of xylitol by weight; and 2) the combination of xylitol and glycerin is present in an amount of about 40% or less by weight based on the combined weight of the xylitol, glycerin, and the total polymer content.

In an aspect of the invention the film product contains citric acid and the plasticizer is a xylitol, wherein 1) the amount of citric acid is about equal to or less than the amount of xylitol by weight; and 2) the xylitol is present in an amount of about 10% to about 40% by weight based on the combined weight of the xylitol and the total polymer content.

In an aspect of the invention the film product contains citric acid and the plasticizer is a combination of xylitol and glycerin, wherein the combination of xylitol, glycerin, and citric acid is present in an amount of about 45% or less by weight based on the combined weight of the xylitol, glycerin, and the total polymer content.

In another embodiment of the present invention, there is provided a film product including: i) about 60% sildenafil citrate; ii) about 18% pullulan; iii) about 0.1 polyethylene oxide; iv) about 5.3% xylitol; v) about 1.5% glycerin; and vi) about 4.7% citric acid; all percentages by weight based on the dry weight of the film product. This embodiment of the invention may further include: at least one sweetener, at least one colorant, at least one emulsifier, and at least one flavor. In this embodiment of the invention, the at least one sweetener is a combination of fructose, sucralose, and maltodextrin; the at least one colorant is a combination of titanium dioxide and FD&C Blue #2; the at least one emulsifier is glyceryl monooleate; and the at least one flavor is mint.

In a further embodiment of the present invention, there is provided a film product including: a. at least one linear polysaccharide; b. a therapeutically effective amount of at least one active component; and c. at least one plasticizer.

As discussed below in the Examples, the Applicants have created a test for estimating the time needed for the film to break when exposed to water. This has been named the Partial Immersion Dissolution (PID) test. Briefly, a film is partially immersed in water and the time from immersion to dissolution is recorded.

In an aspect of the invention the film product has a PID time of about 60 seconds or less, or of about 30 seconds or less, or about 10 seconds or less. In other aspects of the invention the film product has a PID time of about 1 to about 60 seconds, or from about 2 to about 30, or about 2 to about 10 seconds, or about 10 to about 30 seconds.

As discussed below in the Examples, the film products may be tested for tensile strength to determine the force required to break the film when subjected to stress. In an aspect of the invention the film product has a tensile strength of about 0.8 Newton/square millimeter or greater, for example 1.0 N/mm$^2$ or greater.

Optional Components

A variety of other components and fillers may also be added to the films of the present invention. These may include, without limitation, surfactants; other anti-foaming agents; such as simethicone, which promote a smoother film surface by releasing oxygen from the film; thermo-setting gels such as pectin, carageenan, and gelatin, which help in maintaining the dispersion of components; inclusion compounds, such as cyclodextrins and caged molecules, which improve the solubility and/or stability of certain active components; and crystal growth inhibitors, such as hydroxypropylmethylcellulose acetate succinate ("HPMCA") and hydroxypropyl-β-cyclodextrin ("HPCD"), which inhibit the growth of crystals when coupled with appropriate linear polysaccharides of the invention.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, flow accelerators, mold release agents, granulating agents, diluents, binders, buffers, absorbents, glidants, adhesives, anti-adherents, acidulants, softeners, resins, demulcents, solvents, surfactants, emulsifiers; such as glycerol mono oleate, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses, hydroxyalkylceluloses, and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

There may further be added compounds to improve the flow properties of the starch material. Such compounds include animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition.

It is further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinized starches, gelatin, polyvinylpyrrolidone, methylcellulose, sodium carboxymethylcellulose, ethylcellulose, polyacrylamides, polyvinyloxoazolidone, and polyvinylalcohols.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or unstable actives may fit within the hydrophobic cavity, thereby producing an inclusion complex, which is soluble in water. Accordingly, the formation of the inclusion complex permits very insoluble and/or unstable actives to be dissolved in water. A particularly desirable example of such agents are cyclodextrins, which are cyclic carbohydrates derived from starch. Other similar substances, however, are considered well within the scope of the present invention.

Forming the Film

The films of the present invention must be formed into a sheet prior to drying. After the desired components are combined to form a multi-component matrix, including the polymer, water, and an active, and other components as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may use selected materials that are edible or ingestible.

Coating or casting methods are particularly useful for the purpose of forming the films of the present invention. Specific examples include reverse roll coating, forward roll coating, gravure coating, immersion or dip coating, metering rod or Mayer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Mayer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating approaches or is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is circulated back into the reservoir.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

The present invention yields exceptionally uniform film products when attention is paid to reducing the aggregation of the compositional components. By avoiding the introduction of and eliminating excessive air in the mixing process, by selecting polymers and solvents to provide a controllable viscosity, and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition, and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account by the present invention for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_l$) and increase the viscosity of the liquid phase ($\mu$). For an isolated particle, Stokes law relates the terminal settling velocity (Vo) of a rigid spherical body of radius (r) in a viscous fluid, as follows:

$$V_o = (2gr^r)(\rho_p - \rho_t)/9\mu$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analysis has shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as $$v/V_o = 1/(1 + \kappa\varphi)$$

where $\kappa$=a constant, and $\varphi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o = 1 + 2.5\phi$$

where $\mu_o$ is the viscosity of the continuous phase and $\phi$ is the solids volume fraction. At higher volume fractions, the viscosity of the dispersion can be expressed as $$\mu/\mu_o = 1 + 2.5\varphi + C_1\varphi^2 + C_2\varphi^3 + ...$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity, and can impart stability depending on the type of hydrocolloid, its concentration and the particle composition, geometry, size, and volume fraction. The particle size distribution of the dispersed phase needs to be controlled by selecting the smallest realistic particle size in the high viscosity medium, i.e., <500 μm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max} = 3V\mu/2r$$

For pseudoplastic fluids, the viscosity in this shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time periods, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt %, in a viscoelastic fluid matrix with acceptable viscosity values throughout a broad shear rate range. During mixing, pumping, and film casting, shear rates in the range of $10-10^5$ sec.$^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, and structural recovery will influence the quality of the film. As an illustrative example, the leveling of shear-thinning pseudoplastic fluids has been derived as $$\alpha^{(n-1/n)} = \alpha_o^{(n-1/n)} - ((n-1)/)(2n-1))(\tau/K)^{1/n}(2\pi/\lambda)^{(3+n)/n}h^{(2n+1)/n}t$$

where $\alpha$ is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present invention have a very rapid structural recovery, i.e. as the film is formed during processing, it doesn't fall apart or become discontinuous in its structure and compositional uniformity. Such very rapid structural recovery retards particle settling and sedimentation. Moreover, the films or film-forming compositions of the present invention are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of particle size and particle shape is a further consideration. Desirably, the size of the particulate is a particle size of 150 microns or less, for example 100 microns or less. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixing is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients such as drug particles or volatile materials such as flavor oils. The actives are added to smaller mixes of the masterbatch just prior to casting. Thus, the masterbatch pre-mix can be allowed to stand for a longer time without concern for instability in drug or other ingredients.

In embodiments, the multi-component matrix is a polymer matrix, which is then formed into a sheet as described above. In an embodiment, the polymer matrix is a Non-Newtonian visco-elastic polymer matrix. In one embodiment, the polymer matrix is a shear-thinning pseudoplastic fluid when exposed to shear rates of $10-10^5$ sec$^{-1}$.

Drying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be achieved through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Desirably, substantially no air flow is present across the top of the film during its initial setting period, during which a solid, visco-elastic structure is formed. The initial setting period, during which a solid, visco-elastic structure is formed, can take place within the first few minutes, e.g. within about the first 4 minutes or about the first 0.5 to about 4.0 minutes of the drying process.

In embodiments, at least a portion of the solvent is rapidly removed from the matrix to form a visco-elastic film having the active substantially uniformly distributed throughout by rapidly increasing the viscosity of the matrix upon initiation of drying within about 4 minutes to maintain the uniform distribution of the active by locking-in or substantially preventing migration of the active.

Controlling the drying in this manner prevents the destruction and reformation of the film's top surface, which results from conventional drying methods. This is accomplished by placing the liquid visco-elastic composition on the top side of a surface having top and bottom sides. Then, heat is initially applied to the bottom side of the visco-elastic film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

In embodiments of the present invention, any top air flow does not overcome the inherent viscosity of the polymer matrix (e.g., the visco-elastic film) and/or any top air flow is insufficient to cause one or more of the following: (i) surface skinning prior to drying the depth of the film, (ii) surface rippling; (iii) self-aggregation of components; (iv) non-uniformity in the thickness of the film, and (v) non-uniformity of mass per unit volume.

The endogenous or internal temperature of the films should be less than about 100° C., desirably about 90° C. or less, and most desirably about 80° C. or less within the initial setting period (e.g., within about the first 4 minutes of the drying of the film). The temperature inside the drying apparatus (i.e., exogenous to the film) may be any desired temperature and may be well above or below 100° C. In an embodiment of the present invention, the differential in temperature between the endogenous or internal temperature and the temperature inside the drying apparatus is at least about 5° C., preferably from about 5° C. to about 30° C.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

Another method of controlling the drying process involves a zone drying procedure. A zone drying apparatus may include a continuous belt drying tunnel having one or more drying zones located within. The conditions of each drying zone may vary, for example, temperature and humidity may be selectively chosen. It may be desirable to sequentially order the zones to provide a stepped up drying effect.

In aspects of the invention, the speed of the zone drying conveyor desirably is constant. Alternatively, the speed may be altered at a particular stage of the drying procedure to increase or decrease exposure of the film to the conditions of the desired zone. Whether continuous or modified, the zone drying dries the film without surface skinning.

To further control temperature and humidity, the drying zones may include additional atmospheric conditions, such as inert gases. The zone drying apparatus further may be adapted to include additional processes during the zone drying procedure, such as, for example, spraying and laminating processes, so long as controlled drying is maintained in accordance with the invention.

The films may initially have a thickness of about 500 μm to about 1,500 μm, or about 20 mils to about 60 mils, and when dried have a thickness from about 3 μm to about 500 μm, or about 0.1 mils to about 20 mils. Desirably, the dried films will have a thickness of about 1 mils to about 10 mils, more desirably about 2 mils to about 8 mils, and even more desirably, from about 3 mils to about 6 mils.

Testing Films for Uniformity

It may be desirable to test the films of the present invention for chemical and physical uniformity during the film manufacturing process. In particular, samples of the film may be removed and analytically tested for uniformity in film components between various samples. Film thickness and overall appearance may also be checked for physical uniformity. Active uniform films are desired, particularly for films containing pharmaceutical active components due to safety and efficacy reasons.

A method for testing uniformity in accordance with the present invention includes sampling while conveying a film through a manufacturing process. This process may include subjecting the film to drying processes, dividing the film into individual dosage units, and/or packaging the dosages, among others. As the film is conveyed through the manufacturing process, for example on a conveyor belt apparatus, it is cut widthwise into at least one portion. The at least one portion has opposing ends that are separate from any other film portion. For instance, if the film is a roll, it may be cut into separate sub-rolls. Cutting the film may be accomplished by a variety of methods, such as with a knife, razor, laser, or any other suitable means for cutting a film.

The cut film then may be sampled by removing small pieces from each of the opposed ends of the portion(s), without disrupting the middle of the portion(s). Leaving the middle section intact permits the predominant portion of the film to proceed through the manufacturing process without interrupting the conformity of the film and creating sample-inducted gaps in the film. Accordingly, the concern of missing doses is alleviated as the film is further processed, e.g., packaged. Moreover, maintaining the completeness of cut portions or sub-rolls throughout the process will help to alleviate the possibility of interruptions in further film processing or packaging due to quality control issues, for example, alarm stoppage due to notice of missing pieces.

After the end pieces, or sampling sections, are removed from the film portion(s), they may be tested for physical defects in the film and for desired amount of active uniformity in the content of components between samples. Any conventional means for examining and testing the film pieces may be employed, such as, for example, visual inspection, use of analytical equipment, and any other suitable means known to those skilled in the art. Testing for content uniformity of the desired amount of active may be carried out by one or more analytic methods including high pressure liquid chromatography (HPLC) or near-infrared (NIR) spectroscopy. If the testing results show non-uniformity between film samples, the manufacturing process may be altered. For example, the compositional components, compositional rheology, drying conditions, and mixing conditions may be changed. Altering the drying conditions may involve changing the temperature, drying time, film speed through the oven, and dryer positioning, among others.

Moreover, it may be desirable to repeat the steps of sampling and testing throughout the manufacturing process. Testing at multiple intervals may ensure that physically uniform film dosages and film dosages with desired active content uniformity are continuously produced. Alterations to the process can be implemented at any stage to minimize non-uniformity between samples.

In embodiments, the films of the present invention have a substantially uniform content of active by weight per unit volume of the film. In an embodiment, the amount of active in substantially equally sized individual dosage units of the film varies by no more than 10% by weight from a desired amount (e.g., the label claim amount, the dosage amount, etc.). In another embodiment, the amount of active in substantially equally sized individual dosage units of the film varies by no more than 10% between units.

However, it is to be noted that visual inspection and/or comparison or evaluation of the weight of samples of the film product or individual dosage units of the film product alone are not sufficient to demonstrate uniformity of content of the active in the film or individual dosage units of the film product.

As used herein, the term desired amount (e.g., the label claim amount or the dosage amount) of active component per dosage unit means an amount of active component that is intended to be in each dosage unit. In the case of certain products, e.g., pharmaceutical products, there may be an amount of active component claimed on the label of the product. Thus, a desired active component (or drug) label claim per dosage unit means the amount of active component that is claimed to be in each dosage unit based upon the label of the product.

Uniformity of content of active component in a lot may be determined through establishing the amount of active component $(A_{N(i)})$ actually present in each sampled individual dosage unit from the same lot (N) as determined by taking the difference between the amount of active component in the sample with the most amount of active component $(Max_{LOT(N)})$ minus the amount of active component in the sample with the least amount of active component $(Min_{LOT(N)})$ and dividing the difference by the average amount of active component in the lot samples $(Lot_{(N)}$ Sample Average).

$$(Max_{LOT(N)} - Min_{LOT(N)})/\left((A_{N(1)} + A_{N(2)} + + + A_{N(10)})/10\right).$$

Uniformity of content across different lots may be determined through establishing the amount of active component actually present in each of the sampled individual dosage units from the different lots and comparing that amount of active component with a desired amount of active component contained therein. The desired amount of active component, when it is a pharmaceutical, may be referred to as the "label claim amount", thus identifying the amount of pharmaceutical active in the film dosage unit.

In an embodiment, the amount of active in substantially equally sized individual dosage units of the film is not less than 75% or greater than 125% of the desired amount, preferably not less than 85% or greater than 115% of the desired amount.

Using the methods of the present invention, the uniformity of content with respect to desired amount of active is achievable both within individual lots of the film and between different lots of film during large-scale manufacturing of the film. Using the methods of the present invention, this uniformity of content with respect to the amount of active in substantially equally sized individual dosage units is achievable both within individual lots of the film and between different lots of film during large-scale manufacturing of the film.

Uses of Films

The films of the present invention are well suited for many uses. The high degree of desired active uniformity in the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of a desired amount of an active to any of several body surfaces, especially those including mucosal surfaces, such as those found in the oral (i.e., sublingual, lingual, buccal, and gingival), anal, vaginal, ocular, nasal, aural, ophthalmological, and peritoneal environments; the surface of a wound, either on a skin surface or within the body such as during surgery or left in place after surgery to deliver the desired amount of active after the surgical procedure is completed; the surface of an organ (i.e., kidney, lung, liver, heart, etc.), and other similar surfaces.

The films may be used to orally administer an active. This is accomplished by preparing the films as described above and introducing them to the oral cavity of an animal, such as a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films of the present invention takes advantage of the films' tendency to dissolve quickly when introduced to a liquid. An active may be introduced to a liquid by preparing a film in accordance with the present invention, introducing it to a liquid, and allowing it to dissolve. This may be used either to prepare a liquid dosage form of an active, or to flavor a beverage.

The films of the present invention are desirably packaged in sealed, air and moisture resistant packages to protect the active from exposure oxidation, hydrolysis, volatilization and interaction with the environment. Moreover, the films of the present invention dissolve instantly upon contact with saliva or mucosal membrane areas, eliminating the need to wash the dose down with water.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Applicants have developed or employed several subjective and objective tests for evaluation of the robustness of a formulation for high speed production and storage life of the film product.

180 Degree Flex Test

In this test, a film strip is folded end-to-end (180 degrees) and judged for its pliability (softness and flexibility). If the film cracks, it is considered unacceptable as it may break during packaging on the automated line. Pliability of the film is also an important element of patient satisfaction with the dose form because a soft, flexible film strip is easy to apply as compared to a hard, stiff film strip.

Dry Flex

In this test, to stress the film and duplicate the effects of long term storage, all the water is evaporated from the film using a thermal gravimetric balance. The film is then immediately folded using the 180 degree flex test. If the film breaks or cracks it fails.

Folding Endurance

In this test, folding endurance is determined by repeated folding of the strip at the same place until the strip breaks. The number of times the film is folded without breaking is computed as the folding endurance value. A goal of surviving multiple folds (e.g., 180 degrees) without breaking or failing is indicator of the tensile strength and flexibility of the film which is important for taking the high speed route through the packaging machine that the film must endure.

Aged Brittleness

In this test, the film is exposed to room atmosphere, temperature, and humidity, and folded (e.g., 180 degrees) each day to determine if and when the film becomes brittle. This test is a good indicator of long term storage properties of the film.

Dryness Test/Tack Tests

About eight stages of film drying process have been identified and they are set-to-touch, dust-free, tack-free (surface dry), dry-to-touch, dry-hard, dry-through (dry-to-handle), dry-to-recoat and dry print free. Although these tests are primarily used for paint films, most of the studies can be adapted intricately to evaluate pharmaceutical OSF as well. Tack is the tenacity with which the strip adheres to a surface or to its self after being pressed into contact. Two strips are pressed together between the thumb and forefinger using a gloved hand. If the strips stick then they fail if the films come apart without sticking then they pass.

Partial Immersion Dissolution (PID)

This test is used to estimate the time needed for the film to break when exposed to water. This test is applicable to film strips and may be regarded as a surrogate for the disintegration test performed on tablets. In this test, an alligator clamp is attached to the top portion of the film and a weight of 2.8 grams is attached to the bottom portion of the film. The film is gently lowered into a water bath (37.0±0.2° C.) so that half of the film is in the water and the other half remains outside the water. A stopwatch is started at immersion and is stopped when the submerged part of the film dissolves enough to separate from the top half of the film. Experience has shown that the target value for PID depends greatly on the specific application for which the film formulation is designed. Film strips designed for rapid dissolution in the oral cavity or on the oral mucosa generally require a PID value of 2 to 10 seconds. Film strips designed for intermediate dissolution in the oral cavity or on the oral mucosa generally require a PID value of 10 to 30 seconds. PID dissolution is used as a predictive tool for In Vivo dissolution since active containing films cannot easily be tested in vivo due to restrictions on human exposure to active pharmaceuticals.

Tensile Strength

In this test, the tensile strength of the film is measured to determine the force required to break the film when subjected to stress. Testing is performed by mounting opposite ends of the film on clamps of a Texture Analyzer (Texture Technologies Corp. Mode TAXT, Scarsdale, NY). The two clamps are 10-15 mm apart and programmed to separate at a rate of 5 mm/sec to a distance of 20 mm with a trigger force of 5.0 g. The recorded data includes tensile strength, tensile force, and % elongation. Tensile strength is calculated by dividing the resulting force required to break the film (N) by the cross-sectional area of the film (mm$^2$). These measurements are development tools for quantifying and comparing the mechanical strength of various formulations. A tensile strength of 0.8 N/mm$^2$ is considered the lower limit necessary for downstream processing in the automated (commercial) packaging line.

Disintegration Test

In this test, films are evaluated for disintegration time by placing them on the top surface of a beaker of water at 37° C. and evaluating the time taken for the film to break up and start to disperse. No agitation is used in the test and this is a pure test of wetting and diffusion.

Shock Sensitivity

In this test, a die of the correct size made by DieMasters (Pacific Missouri) is used with compression to cut the sheet into individual dose form. The film edges are visually observed for irregularities after cutting the strips into the final size. If the edges are clean (like a cut piece of paper) then the film passes. If the edges are jagged and irregular then the film fails. This subjective test is an indicator of films that will create production slowdowns during a high speed packaging process.

Examples 1-22

Twenty two film formulations were prepared (Examples 1-22) and tested as shown below. These films included various plasticizers or combinations of plasticizers as shown in Table 1. These plasticizers were Sorbitol, erythritol, glycerin, xylitol, citric acid, PEG, propylene glycol, dextrose, and maltitol. The below ingredients were added to a fabricated glass bowl and mixed using a Degussa Dental Multivac Stirrer which was equipped with a gate impeller. The ingredients were mixed to form a coating solution as follows:

1. Pullulan*
   *Total % of Pullulan+Plasticizer=32.435%
2. Plasticizer (Table 1)**
   ** Plasticizers used were added as w/w % of dry polymer weight+ plasticizer
3. Antifoaming agent (0.065%)
4. Distilled Water (67.5%)

TABLE 1

Film Composition for Pullulan/Plasticizer Evaluation (numerical values for the plasticizers refer to the w/w % based on the polymer dry weight + plasticizer)

| | | | | | | | Propylene | | |
|---|---|---|---|---|---|---|---|---|---|
| Example | Sorbitol | Erythritol | Glycerin | Xylitol | Citric Acid | PEG | Glycol | Dextrose | Maltitol |
| 1 | | 30 | | | | | | | |
| 2 | 30 | | | | | | | | |
| 3 | | | 15 | | | | | | |
| 4 | | 30 | 10 | | | | | | |
| 5 | | 26.5 | 8.75 | | | | | | |
| 6 | | | | 30 | | | | | |
| 7 | | | | | | | 30 | | |
| 8 | | | | | 10 | | | | |
| 9 | | | 30 | | | | | | |
| 10 | | | 15 | 15 | | | | | |
| 11 | | | | 20 | 10 | | | | |
| 12 | | | 20 | | 10 | | | | |
| 13 | | | 10 | 10 | 10 | | | | |
| 14 | | | 22.5 | | | | | | |
| 15 | | | | | | | | | 30 |
| 16 | | | | | | 30 | | | |
| 17 | | | | | | | | 30 | |
| 18 | | | | | 10 | | | | |
| 19 | | | | | 40 | | | | |
| 20 | | | | | | | | 10 | |
| 21 | | | | | | | | 40 | |
| 22 | | | 18.75 | | | | | | |

The ingredients were mixed under a vacuum to form a coating solution according to the following schedule:

| 20 Minutes | Stirring = 125 rpm | Vacuum = 60% (18 in Hg) |
| 20 Minutes | Stirring = 125 rpm | Vacuum = 90% (26 in Hg) |
| 20 Minutes | Stirring = 125 rpm | Vacuum = 95% (27 in Hg) |
| 12 Minutes | Stirring = 125 rpm | Vacuum = 98% (28 in Hg) |
| 8 Minutes | Stirring = 125 rpm | Vacuum = 100% (29 in Hg) |

The coating solution was cast into wet film using the K-Control Coater with the micrometer adjustable wedge bar set at 500 microns onto Mylar substrate. The cast wet film was dried for 18 minutes in an 80° C. convection air oven. The dried film had 1.33% moisture content. The percent moisture was determined using a Mettler HR73 Moisture Analyzer. The film had a thickness of 3.5 to 4 mils.

The film was observed for flexibility out of the oven and out of the moisture analyzer after completely drying. The film was also observed subjectively for strength by pulling on the film.

The film was allowed to stand overnight in room atmosphere. After standing overnight, the film was cut into 18 mm×22 mm strips using a steel rule die fabricated by DieMasters. The strips were observed for shock sensitivity and tackiness. A 360 degree bend test was run on a film strip to determine whether the film strip fails at less than 100 bends. The Partial Immersion Dissolution (PID) was measured on a 45 to 50 mg strip using 37° C. water.

Films that passed the initial testing were allowed to sit at room temperature and room atmospheric conditions and tested over time to observe any brittleness with aging.

The results of the testing are shown in Table 2.

3. 18.5 g of Maltitol Syrup
4. 1.8 g (3.000%) Artificial Sweetener
5. 2.4 g (4.000%) Flavoring Agent
6. 0.3 g (0.500%) Antifoaming Agent
7. 0.024 g Colorant
8. 135.375 g Distilled Water Ingredients 1,3, and 6 were mixed together with a spatula in a fabricated glass bowl. Ingredients 7 and 8 were then added to the bowl and mixed further with a spatula. A coating solution was prepared from this mixture as described below using the Degussa Dental Multivac Compact.

The mixture was stirred for 44 minutes at 125 rpm under a vacuum (100% (29 in Hg)). Distilled water was added to obtain QS. A blend of ingredients 2 and 4 was then added to the bowl. Stirring was continued for another 20 minutes at 125 rpm under a vacuum (60% (18.5 in Hg)). Stirring was continued for another 60 minutes at 125 rpm under a vacuum (100% (29 in Hg)). Distilled water was added to obtain QS. Stirring was continued for another 4 minutes at 125 rpm under a vacuum (100% (29 in Hg)). The mixture was then allowed to stand for 80 minutes without stirring or vacuum. Distilled water was added to obtain QS. Ingredient 5 was then added. The mixture was then stirred for 8 minutes at 125 rpm under a vacuum (100%(29 in Hg)) to form the coating solution.

The coating solution was cast into wet film using the K-Control Coater with the micrometer adjustable wedge bar set at 200, 400, 600, 800, and 1000 microns onto Mylar substrate. The wet films were dried for 18 to 30 minutes depending on the micrometer wedge bar setting in an 80° C. convection air oven. The dried films had a % moisture content of 0.79% to 2.21% when tested using the Mettler

TABLE 2

| | Evaluation of Plasticizers on Pullulan Film Properties. | | | | | | |
|---|---|---|---|---|---|---|---|
| | Film Properties Analysis | | | | | | |
| Example | Tack | Initial Flex | Dry Flex | Strength | Initial Brittleness | Aged Brittleness | Bend Test | Shock Sensitive |
| 1 | Sticky | P | P | Good | P | F | N/A | F |
| 2 | Sticky | P | P | Good | P | F | N/A | F |
| 3 | Not Stick | F | F | Good | F | N/A | N/A | F |
| 4 | Sticky | P | P | Good | P | F | N/A | F |
| 5 | Sticky | P | P | Good | P | F | N/A | F |
| 6 | Not Stick | P | P | Good | P | P (22 days) | P | Slight |
| 7 | Not Stick | F | F | N/A | F | F | N/A | F |
| 8 | Not Stick | P | F | N/A | P | F | N/A | N/A |
| 9 | Sticky | P | P | N/A | P | P | P | P |
| 10 | Not Stick | P | P | Good | P | P | P | P |
| 11 | Not Stick | P | P | N/A | P | F | F | F |
| 12 | Sticky | P | P | N/A | P | P | P | P |
| 13 | Not Stick | P | P | N/A | P | P | P | P |
| 14 | Sticky | P | P | Good | P | P | P | P |
| 15 | Not Stick | F | F | N/A | F | N/A | N/A | F |
| 16 | Not Stick | F | F | N/A | F | N/A | N/A | F |
| 17 | Not Stick | F | F | N/A | F | N/A | N/A | N/A |
| 18 | Not Stick | F | F | N/A | F | F | N/A | N/A |
| 19 | Sticky | P | P | N/A | P | P (22 days) | N/A | N/A |
| 20 | Not Stick | F | F | N/A | F | F | N/A | N/A |
| 21 | Sticky | P | P | N/A | P | F | N/A | N/A |
| 22 | Not Stick | P | P | Good | P | P | P | P |

Comparative Examples 23-27

Comparative film compositions were prepared using the ingredients and protocol shown below.

Ingredients:
1. 27.75 g (46.25%) HPMC
2. 13.875 g (23.125%) Polyethylene Oxide

HR73 Moisture Analyzer. The films had a thickness of 1.9 to 8 mils. The dried films were cut into 22 mm×20 mm strips which had a weight range of 18 to 97 mg.

The dried film strips were tested for Partial Immersion Dissolution at 37° C. and dispersion time after placing on top of 37° C. water in a 500 ml beaker without stirring. The results are shown in Table 3.

TABLE 3

Dissolution Testing of HPMC/PEO/Maltitol
Based Film* Strips (22 mm × 20 mm)

| Example No. | Film Thickness | Strip Weight (mg) | PID 37° C. | Dispersion Time in 37° C. Water Without Stirring |
|---|---|---|---|---|
| 23 | 1.9 mils | 18 mg | 1.4 sec. | 22.3 sec. |
| 24 | 3.3 mils | 36 mg | 9.4 sec. | 3 min 53 sec. |
| 25 | 4.75 mils | 56 to 57 mg | 24.0 sec. | 9.0 min. |
| 26 | 6.15 mils | 78 to 79 mg | 46.0 sec | 20.0 min |
| 27 | 8.0 mils | 95 to 97 mg | 1 min. 8 sec. | 20 min. 23 sec. |

Examples 28-32

Film products of the invention were prepared using the ingredients and protocol shown below.

Ingredients:
1. 33.67 g (64.75%) Pullulan
2. 7.215 g (13.875%) Xylitol
3. 7.215 g (13.875%) Glycerin
4. 1.56 g (3.000%) Artificial Sweetener
5. 2.08 g (4.000%) Flavoring Agent
6. 0.26 g (0.500%) Antifoaming Agent
7. 0.021 g Colorant
8. 108 g Distilled Water Ingredients 1, 2, 3, 4, 6, 7, and 8 were added to a fabricated glass bowl. The coating solution was prepared as described below using the Degussa Dental Multivac Compact. The mixture was stirred for 20 minutes at 125 rpm under a vacuum (60% (18.5 in Hg)). The mixture was then stirred for 20 minutes at 125 rpm under a vacuum (90% (26 in Hg)). The mixture was then stirred for 20 minutes at 125 rpm under a vacuum (95% (27 in Hg)). The mixture was then stirred for 12 minutes at 125 rpm under a vacuum (98% (28 in Hg)). Distilled water was added to obtain QS. Ingredient 5 was added. The mixture was then stirred for 8 minutes at 125 rpm under a vacuum (100% (29 in Hg)) to form a coating solution.

The coating solution was cast into wet film using the K-Control Coater with the micrometer adjustable wedge bar set at 200, 360, 560, 780, and 950 microns onto Mylar substrate. The wet films were dried for 15 to 34 minutes depending on the micrometer wedge bar setting in an 80° C. convection air oven. The dried films had % moisture of 1.44% to 2.80% when tested using the Mettler HR73 Moisture Analyzer. The dried films had a thickness of 1.35 to 6.3 mils. The dried films were cut into 22 mm×20 mm strips which had a weight range of 18 to 97 mg. The dried film strips were tested for Partial Immersion Dissolution at 37° C. and dispersion time after placing on top of 37° C. water in a 500 ml beaker without stirring. The results are shown in Table 4

TABLE 4

Dissolution Testing on Pullulan/Xylitol/Glycerin
Based Film** Strips (22 × 20 mm)

| Example No. | Film Thickness | Strip Weight (mg) | PID 37° C. | Dispersion Time in 37° C. Water Without Stirring |
|---|---|---|---|---|
| 28 | 1.35 mils | 18 to 19 mg | 0.8 sec. | 4.1 sec. |
| 29 | 2.6 mils | 35 to 37 mg | 3.06 sec. | 6.5 sec. |
| 30 | 4.3 mils | 56 to 58 mg | 5.8 sec. | 23.6 sec. |

TABLE 4-continued

Dissolution Testing on Pullulan/Xylitol/Glycerin
Based Film** Strips (22 × 20 mm)

| Example No. | Film Thickness | Strip Weight (mg) | PID 37° C. | Dispersion Time in 37° C. Water Without Stirring |
|---|---|---|---|---|
| 31 | 5.25 mils | 77 to 79 mg | 10.3 sec. | 33.0 sec. |
| 32 | 6.3 mils | 95 to 97 mg | 15.2 sec. | 3 min. 44.0 sec. |

Figure 2:
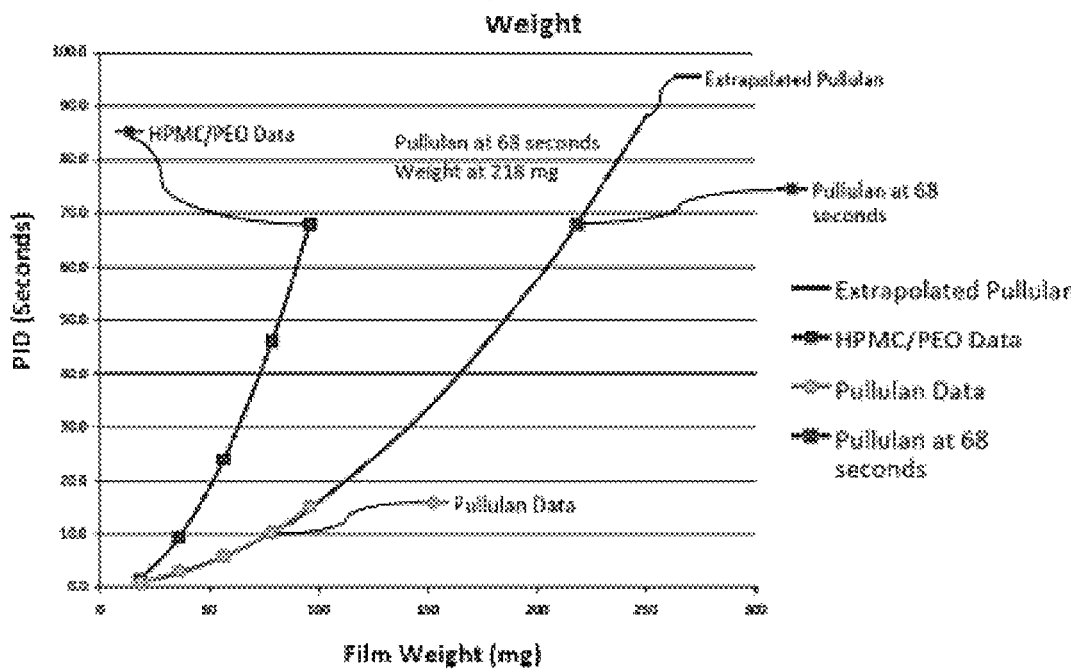
FIG. 2 shows the partial immersion dissolution time data for the comparative film compositions and inventive film products and includes an extrapolation of the partial immersion dissolution time for greater weights of film.
Figure 3:
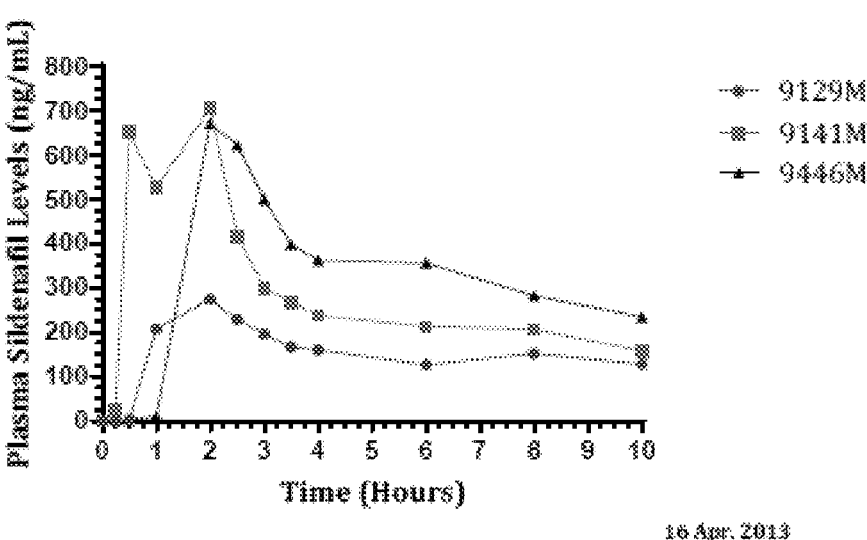
FIG. 3 shows the plasma sildenafil levels for individual dogs dosed with a 50 mg Viagra™ tablet.
Figure 4:
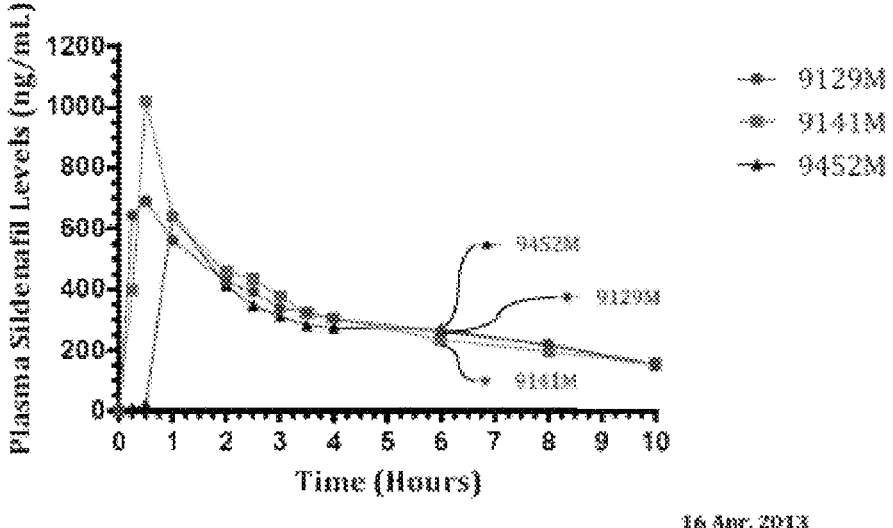
FIG. 4 shows the plasma sildenafil levels for individual dogs dosed with a film product of the invention containing sildenafil citrate in a 50 mg base equivalent amount.
Figure 5:
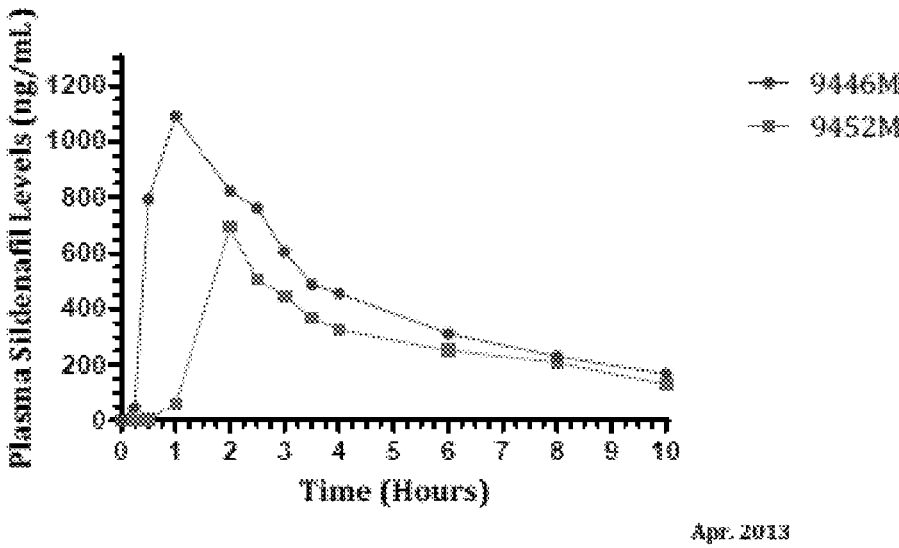
FIG. 5 shows the plasma sildenafil levels for individual dogs dosed with a film product of the invention containing sildenafil citrate in a 50 mg base equivalent amount in a gelatin capsule.
Figure 6:
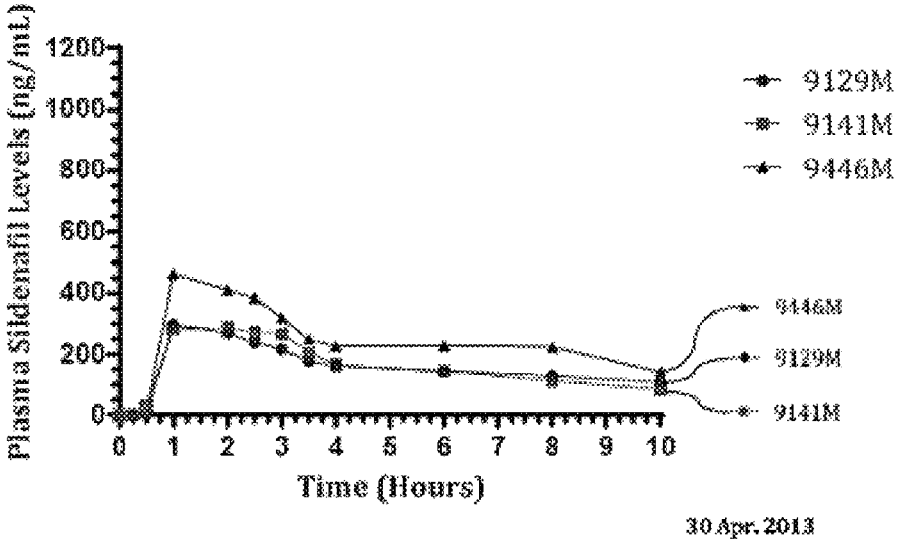
FIG. 6 shows the plasma sildenafil levels for individual dogs dosed with a film product of the invention containing sildenafil resinate in a 50 mg base equivalent amount.
Figure 7:
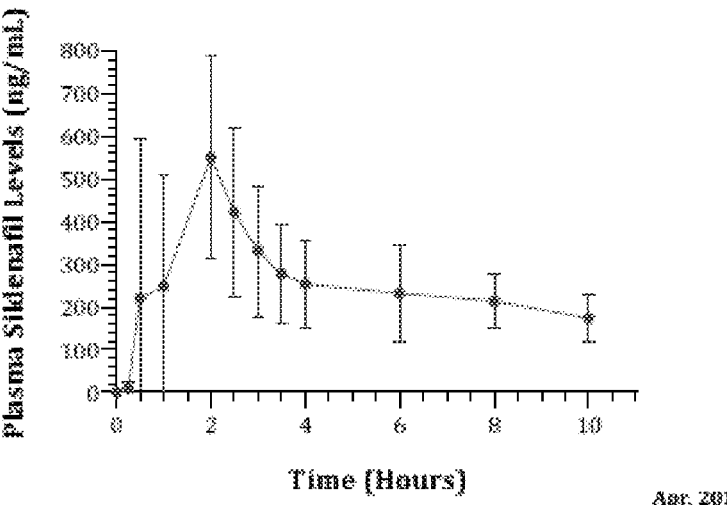
FIG. 7 shows the mean plasma sildenafil levels for dogs dosed with a 50 mg Viagra™ tablet.
Figure 8:
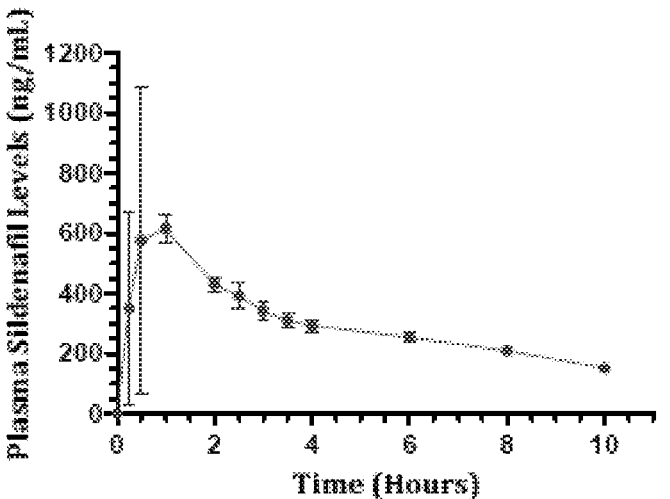
FIG. 8 shows the mean plasma sildenafil levels for dogs dosed with a film product of the invention containing sildenafil citrate in a 50 mg base equivalent amount.
Figure 9:
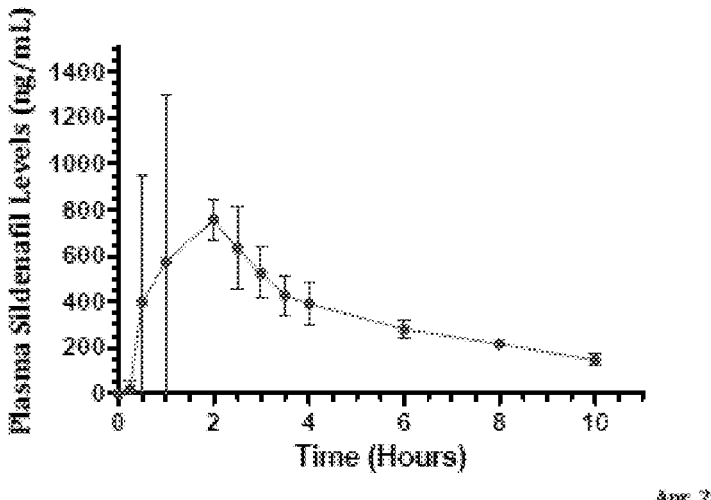
FIG. 9 shows the mean plasma sildenafil levels for dogs dosed with a film product of the invention containing sildenafil citrate in a 50 mg base equivalent amount in a gelatin capsule.
Figure 10:
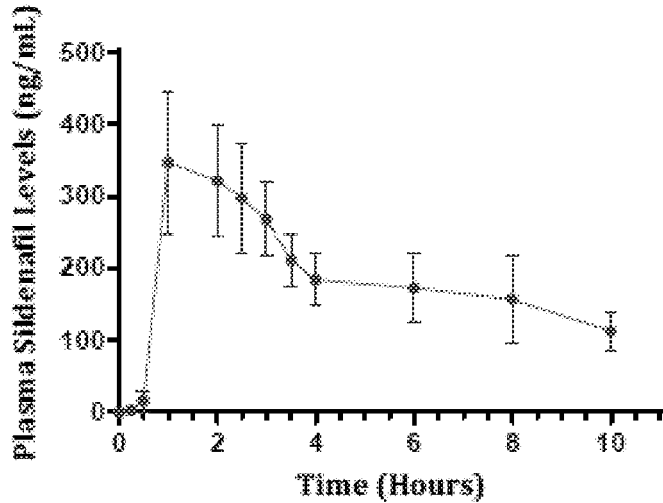
FIG. 10 shows the mean plasma sildenafil levels for dogs dosed with a film product of the invention containing sildenafil resinate in a 50 mg base equivalent amount.

FIG. 1 shows a comparison of the partial immersion dissolution time for the comparative film compositions (HPMC/PEO) and inventive film products (Pullulan). FIG. 2 shows the partial immersion dissolution time data for the comparative film compositions and inventive film products and includes an extrapolation of the partial immersion dissolution time for greater weights of film. Based on the examples, the use of xylitol and glycerol, alone or combined, with or without citric acid, produces OSF that pass all the subjective tests for high speed film production and packaging and storage. Moreover, such films have the ability to load higher amounts of active pharmaceutical ingredient per film and still allow dissolution at a faster PID time when compared to traditional OSF polymer formulations. Four to five times more film weight may be loaded into the same size film (area) and while still maintaining the PID time when compared to a traditional polymer film formulation. Moreover, these data demonstrate that there is a preferred range for these plasticizers in the film product.

Examples 33-38

Film products of the invention were prepared as described above with the ingredients set forth in the tables below.

Example 33: Sildenafil Citrate 70 mg (50 mg Sildenafil Base Equivalent)

TABLE 5

Film product of the invention with
50 mg Sildenafil base equivalent.

| Composition | Dry Basis (% w/w) | Dry Basis (mg/film) | Wet Basis (% w/w) | Weight Charged (g) |
|---|---|---|---|---|
| Sildenafil Citrate | 61.508 | 70.008 | 31.463 | 26.086 |
| Monosaccharide Sweetener | 0.545 | 0.620 | 0.279 | 0.231 |
| Pullulan | 16.454 | 18.728 | 8.417 | 6.979 |
| Xylitol | 5.328 | 6.064 | 2.725 | 2.259 |
| Artificial Sweetener | 0.679 | 0.773 | 0.347 | 0.288 |
| Starch Derivative | 1.044 | 1.188 | 0.534 | 0.443 |
| Glycerin | 1.565 | 1.781 | 0.800 | 0.663 |
| Antifoaming Agent | 1.565 | 1.781 | 0.800 | 0.663 |
| Opacifier | 2.216 | 2.522 | 1.133 | 0.939 |
| Polyether | 0.283 | 0.322 | 0.145 | 0.120 |
| Citric Acid | 4.715 | 5.367 | 2.412 | 2.000 |
| Colorant | 0.071 | 0.081 | 0.036 | 0.030 |
| Flavoring Agent | 4.027 | 4.584 | 2.060 | 1.708 |
| Sum | | 113.819 | 51.151 | 42.409 |
| Water Purified | | 4.101 | 48.849 | 40.499 |
| Total | 100.000 | 117.920 | 100.000 | 82.908 |

The film product of Example 33 had the physical data shown in Table 6 (below).

TABLE 6

Physical data a film product of the invention with
50 mg Sildenafil base equivalent (Example 33).

| Physical Data 50 mg Example Storage conditions | | PID (sec) | Tensile Data* N/mm |
|---|---|---|---|
| Initial analysis | | 6 | 1.460 |
| 25° C./60% RH | 2 weeks | 6 | NT |
| | 3 weeks | NT | 1.196 |
| | 4 weeks | 6 | 2.431 |
| | 3 months | 6 | 1.607 |
| 40° C./75% RH | 1 week | 7 | 1.139 |
| | 2 weeks | 6 | NT |
| | 3 weeks | NT | 5.363 |
| | 4 weeks | 6 | 2.657 |
| | 3 months | 5 | 2.062 |

Example 34: Sildenafil Citrate 140 mg (100 mg Sildenafil Base Equivalent)

TABLE 7

Film product of the invention with
100 mg Sildenafil base equivalent.

| Component | Dry Basis (% w/w) | Dry Basis (mg/film) | Wet Basis (% w/w) | Weight Charged (g) |
|---|---|---|---|---|
| Sildenafil Citrate | 63.283 | 140.001 | 32.384 | 26.846 |
| Monosaccharide Sweetener | 0.542 | 1.199 | 0.277 | 0.230 |
| Pullulan | 14.000 | 30.972 | 7.164 | 5.939 |
| Xylitol | 5.327 | 11.785 | 2.726 | 2.260 |
| Artificial Sweetener | 0.679 | 1.502 | 0.347 | 0.288 |
| Starch Derivative | 1.045 | 2.312 | 0.535 | 0.444 |
| Glycerin | 1.565 | 3.462 | 0.801 | 0.664 |
| Antifoaming Agent | 1.565 | 3.462 | 0.801 | 0.664 |
| Opacifier | 2.216 | 4.902 | 1.134 | 0.940 |
| Polyether | 1.000 | 2.212 | 0.512 | 0.424 |
| Citric Acid | 4.691 | 10.378 | 2.401 | 1.990 |
| Colorant | 0.073 | 0.161 | 0.037 | 0.031 |
| Flavoring Agent | 4.014 | 8.880 | 2.054 | 1.703 |
| Sum | | 221.228 | 51.173 | 42.423 |
| Water Purified | | 7.962 | 48.827 | 40.478 |
| Total | 100.000 | 229.190 | 100.000 | 82.901 |

Example 35: Sildenafil Citrate 140 mg (1100 mg Sildenafil Base Equivalent)

TABLE 8

Film product of the invention with
100 mg Sildenafil base equivalent.

| Component | Dry Basis (% w/w) | Dry Basis (mg/film) | Wet Basis (% w/w) | Weight Charged (g) |
|---|---|---|---|---|
| Sildenafil Citrate | 60.183 | 140.004 | 30.789 | 25.524 |
| Monosaccharide Sweetener | 0.542 | 1.261 | 0.277 | 0.230 |
| Pullulan | 18.000 | 41.873 | 9.209 | 7.634 |
| Xylitol | 5.328 | 12.395 | 2.726 | 2.260 |
| Artificial Sweetener | 0.679 | 1.580 | 0.347 | 0.288 |
| Starch Derivative | 1.044 | 2.429 | 0.534 | 0.443 |
| Glycerin | 1.565 | 3.641 | 0.801 | 0.664 |
| Antifoaming Agent | 1.565 | 3.641 | 0.801 | 0.664 |
| Opacifier | 2.216 | 5.155 | 1.134 | 0.940 |
| Polyether | 0.100 | 0.233 | 0.051 | 0.042 |

TABLE 8-continued

Film product of the invention with
100 mg Sildenafil base equivalent.

| Component | Dry Basis (% w/w) | Dry Basis (mg/film) | Wet Basis (% w/w) | Weight Charged (g) |
|---|---|---|---|---|
| Citric Acid | 4.691 | 10.913 | 2.400 | 1.990 |
| Colorant | 0.073 | 0.170 | 0.037 | 0.031 |
| Flavoring Agent | 4.014 | 9.338 | 2.054 | 1.702 |
| Sum | | 232.633 | 51.160 | 42.412 |
| Water Purified | | 8.367 | 48.840 | 40.488 |
| Total | 100.000 | 241.000 | 100.000 | 82.900 |

Example 36: Sildenafil Citrate 140 mg (100 mg Sildenafil Base Equivalent)

TABLE 9

Film product of the invention with
100 mg Sildenafil base equivalent.

| Component | Dry Basis (% w/w) | Dry Basis (mg/film) | Wet Basis (% w/w) | Weight Charged (g) |
|---|---|---|---|---|
| Sildenafil Citrate | 64.184 | 140.004 | 32.867 | 27.247 |
| Monosaccharide Sweetener | 0.542 | 1.182 | 0.277 | 0.230 |
| Pullulan | 14.000 | 30.538 | 7.169 | 5.943 |
| Xylitol | 5.327 | 11.620 | 2.728 | 2.262 |
| Artificial Sweetener | 0.679 | 1.481 | 0.348 | 0.288 |
| Starch Derivative | 1.044 | 2.277 | 0.535 | 0.444 |
| Glycerin | 1.565 | 3.414 | 0.801 | 0.664 |
| Antifoaming agent | 1.565 | 3.414 | 0.801 | 0.664 |
| Opacifier | 2.216 | 4.834 | 1.135 | 0.941 |
| Polyether | 0.100 | 0.218 | 0.051 | 0.042 |
| Citric Acid | 4.691 | 10.232 | 2.402 | 1.991 |
| Colorant | 0.073 | 0.159 | 0.037 | 0.031 |
| Flavoring Agent | 4.014 | 8.756 | 2.056 | 1.704 |
| Sum | | 218.129 | 51.207 | 42.451 |
| Water Purified | | 7.851 | 48.793 | 40.449 |
| Total | 100.000 | 225.980 | 100.000 | 82.900 |

Example 37: Sildenafil Citrate 140 mg (100 mg Sildenafil Base Equivalent)

TABLE 10

Film product of the invention with
100 mg Sildenafil base equivalent.

| Composition | Dry Basis (% w/w) | Dry Basis (mg/film) | Wet Basis (% w/w) | Weight Charged (g) |
|---|---|---|---|---|
| Sildenafil Citrate | 59.284 | 140.005 | 30.337 | 25.149 |
| Monosaccharide Sweetener | 0.542 | 1.280 | 0.277 | 0.230 |
| Pullulan | 18.000 | 42.509 | 9.211 | 7.636 |
| Xylitol | 5.327 | 12.580 | 2.726 | 2.260 |
| Artificial Sweetener | 0.679 | 1.604 | 0.348 | 0.288 |
| Starch Derivative | 1.044 | 2.466 | 0.534 | 0.443 |
| Glycerin | 1.565 | 3.696 | 0.801 | 0.664 |
| Antifoaming Agent | 1.565 | 3.696 | 0.801 | 0.664 |
| Opacifier | 2.216 | 5.233 | 1.134 | 0.940 |
| Polyether | 1.000 | 2.362 | 0.512 | 0.424 |

TABLE 10-continued

| | Film product of the invention with 100 mg Sildenafil base equivalent. | | | |
|---|---|---|---|---|
| Composition | Dry Basis (% w/w) | Dry Basis (mg/film) | Wet Basis (% w/w) | Weight Charged (g) |
| Citric Acid | 4.691 | 11.078 | 2.400 | 1.990 |
| Colorant | 0.073 | 0.172 | 0.037 | 0.031 |
| Flavoring Agent | 4.014 | 9.479 | 2.054 | 1.703 |
| Sum | | 236.160 | 51.172 | 42.422 |
| Water Purified | | 8.500 | 48.828 | 40.478 |
| Total | 100.000 | 244.660 | 100.000 | 82.900 |

Example 38: Loratadine 100 mg

TABLE 11

| | Film product of the invention with 100 mg loratadine. | |
|---|---|---|
| Ingredient | Dry Basis (% w/w) | Dry Basis (mg/film) |
| Pullulan | 27.94* | 46.58 |
| Xylitol | 5.99* | 9.98 |
| Glycerin | 5.99* | 9.98 |

TABLE 11-continued

| | Film product of the invention with 100 mg loratadine. | |
|---|---|---|
| Ingredient | Dry Basis (% w/w) | Dry Basis (mg/film) |
| Antifoaming Agent | 0.08 | 0.13 |
| Loratadine | 60.00 | 100.00 |
| Total | 100 | 166.67 |

Comparative Example 39: Loratadine 100 mg in HPMC/PEO Formulation

TABLE 12

| | Comparative film with 100 mg loratadine. | |
|---|---|---|
| Ingredient | Dry Basis (% w/w) | Dry Basis (mg/film) |
| HPMC | 19.96 | 33.28 |
| Maltitol | 9.98 | 16.63 |
| PEO | 9.98 | 16.63 |
| Antifoaming Agent | 0.08 | 0.13 |
| Loratadine | 60.00 | 100.00 |
| Total | 100 | 166.67 |

Examples 38 and 39 were the same size and weight—22 mm×20 mm and 166.67 mg.

Table 13 below shows the percent of plasticizer, polymer, and acid for Examples 33-38 and provides the weight ratio of the combination of the plasticizer and acid to the combined weight of the plasticizer, acid, and polymer.

TABLE 13

| | | Plasticizer, Acid, Polymer comparison. | | | | |
|---|---|---|---|---|---|---|
| Example | Polymer Wt. % | Plasticizer Wt. % Xylitol | Glycerin | Citric Acid | Total Plasticizer Wt. % | Plasticizer and Acid W/W % of Polymer + Acid + Plasticizer |
| 33 | 17.5 | 5.33 | 1.57 | 4.72 | 11.62 | 39.9 |
| 34 | 16 | 5.33 | 1.57 | 4.69 | 11.59 | 42 |
| 35 | 19.1 | 5.33 | 1.57 | 4.69 | 11.59 | 37.8 |
| 36 | 15.1 | 5.33 | 1.57 | 4.69 | 11.59 | 43.4 |
| 37 | 20 | 5.33 | 1.57 | 4.69 | 11.59 | 36.7 |
| 38 | 27.94 | 5.99 | 5.99 | | 11.98 | 30 |

Table 14 below shows the content uniformity and physical testing data for the 100 mg sildenafil based equivalent film products of Examples 34-37.

TABLE 14

| | Content uniformity and physical testing data for 100 mg sildenafil base equivalent film products. | | | | | | |
|---|---|---|---|---|---|---|---|
| Example | Content Uniformity (n = 10)* Mean | Min | Max | RSD % | PID (n = 3) | Tensile Strength (n = 3) @ 35% RH N/mm$^2$ | % Elongation @ max force @ 35% RH |
| 34 | 101.7 | 98.5 | 103.5 | 1.6 | 12 | 1.44 | 7.37 |
| 35 | 101.4 | 98.4 | 105.1 | 2.0 | 24 | 3.01 | 4.62 |
| 36 | 106.7 | 104.9 | 108.2 | 1.0 | 14 | 1.65 | 4.71 |
| 37 | 105.8 | 103.0 | 108.6 | 1.4 | 29 | 2.15 | 4.54 |

Based on the 140 mg sildenafil citrate examples, Example 34 is the most desirable formulation in terms of content uniformity, PID, Tensile Strength, and Elongation studies.

Table 15 below shows the physical testing data for the Examples 34, 38, and 39. As can be seen from the comparison of Example 38 (inventive) to Example 39 (comparative) the inventive film product was found satisfactory in all of the tested physical parameters. The comparative film product, on the other hand, was unsatisfactory in many parameters. Moreover the inventive film product of Example 38 has a PID over 6 times faster than that of the comparative film product of Example 39.

TABLE 15

Physical testing data for Examples 34, 38, and 39.

| Example | Tack | Initial Flex | Dry Flex | Strength | Initial Brittleness | Aged Brittleness | Bend Test | Shock Sensitive | PID (sec) |
|---|---|---|---|---|---|---|---|---|---|
| 34 | Not Tacky | P | P | Good | P | P | P | P | 12 |
| 38* | Not Tacky | P | P | Good | P | N/A | P | P | 29 |
| 39* | Not Tacky | F | F | Good | F | N/A | N/A | P | 193 |

*Examples 38 and 39 were the same size and weight (22 mm × 20 mm; 166.67 mg).

Pharmacokinetic Testing

Film products of the invention were tested against Viagra™ Tablets for plasma sildenafil levels. In particular, a 50 mg Viagra™ tablet was tested against film products of the invention including 50 mg base equivalent of sildenafil as sildenafil citrate or sildenafil resinate. The test articles were as follows: 1) 50 mg Viagra™ tablet, 2) 50 mg base equivalent sildenafil citrate film product of the invention, 3) 50 mg base equivalent sildenafil citrate film product of the invention in a gelatin capsule, and 4) 50 mg base equivalent sildenafil resinate film product of the invention. In each instance the test article was placed in the back of the mouth of beagle dogs.

Blood was collected from the beagle dogs at various times and analyzed for the plasma level of sildenafil.

Figure 11:
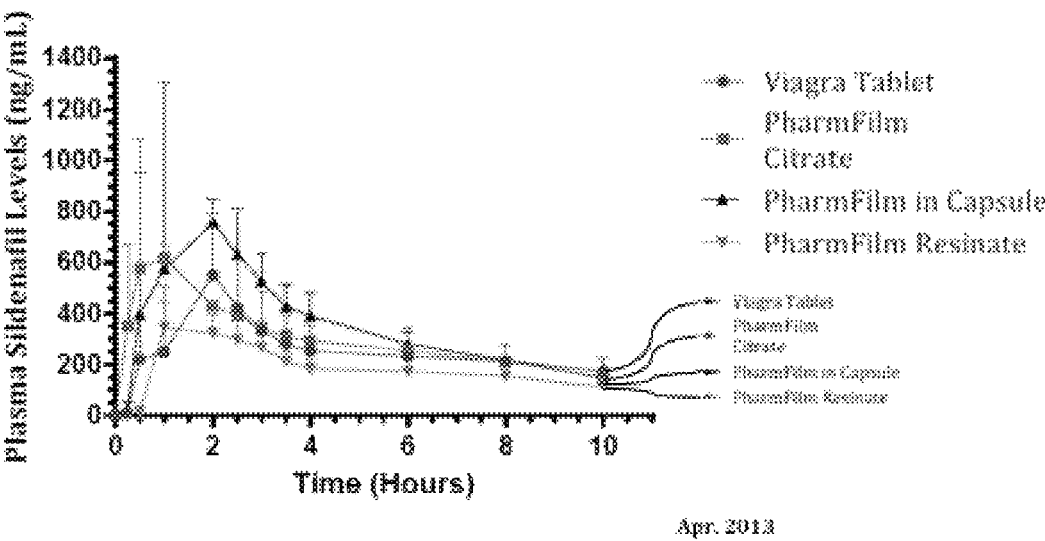
FIG. 11 shows a comparison of the mean plasma sildenafil levels for dogs dosed with a 50 mg Viagra™ tablet, dogs dosed with a film product of the invention containing sildenafil citrate in a 50 mg base equivalent amount, dogs dosed with a film product of the invention containing sildenafil citrate in a 50 mg base equivalent amount in a gelatin capsule, and dogs dosed with a film product of the invention containing sildenafil resinate in a 50 mg base equivalent amount from dosing to 10 hours post-dosing.
Figure 12:
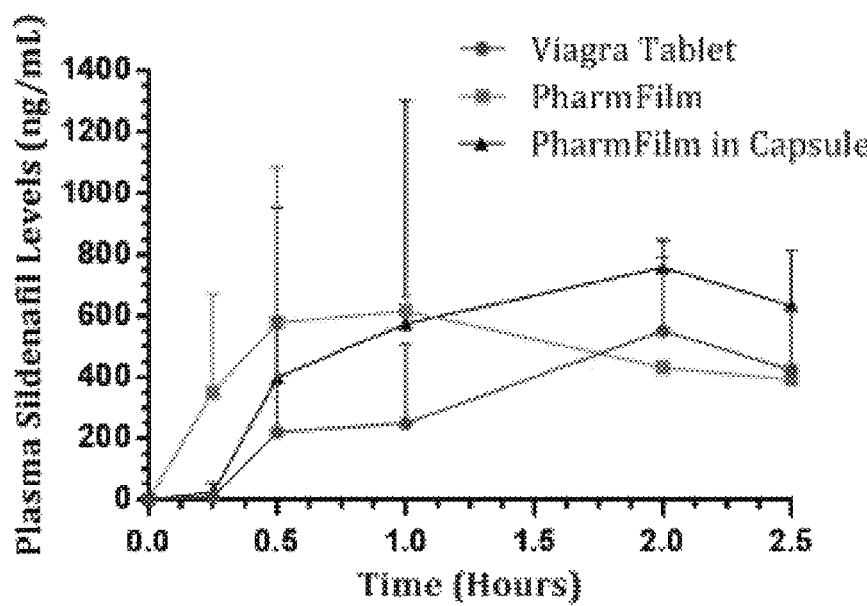
FIG. 12 shows a comparison of the mean plasma sildenafil levels for dogs dosed with a 50 mg Viagra™ tablet, dogs dosed with a film product of the invention containing sildenafil citrate in a 50 mg base equivalent amount, and dogs dosed with a film product of the invention containing sildenafil citrate in a 50 mg base equivalent amount in a gelatin capsule from dosing to 2.5 hours post-dosing.

The results are shown in FIGS. 3-11. In particular, FIGS. 3-6 show the plasma sildenafil levels for individual dogs for each of the 4 test articles, respectively. FIGS. 7-10 show the mean plasma sildenafil levels for each of the 4 test articles, respectively. FIGS. 11 and 12 show a comparison of the mean plasma sildenafil levels for the test articles.

The test articles had the following pharmacokinetic profiles:

TABLE 16

Pharmacokinetic testing results for sildenafil citrate film, 50 mg VIAGRA ™ tablet, and an oral solution of sildenafil citrate.

| Dosage Form | $AUC_{0\text{-}30\,min}$ (ng/ml · hr) | $AUC_{0\text{-}2\,hr}$ (ng/ml · hr) | $AUC_{0\text{-}10\,hr}$ (ng/ml · hr) | $C_{MAX}$ (ng/mL) | $T_{MAX}$ (Minutes) |
|---|---|---|---|---|---|
| VIAGRA ™ Tablet | 29.62 | 546.6 | 2584 | 550.7 | 120 |
| Sildenafil Citrate Film | 160.0 | 982.1 | 3062 | 616.3 | 30 |
| Sildenafil Citrate Film/Capsule[†] | 55.52 | 964.9 | 3581 | 758.0 | 120 |
| 0.1N HCl Solution* at 1.0 mg/kg (Normalized to 4 mg/kg) | N/A | N/A | 842 (3368) | 117 (468) | 66 (median) |

[†]Average dose about 4.0 mg/kg.

*Walker, et al., "Pharmacokinetics and Metabolism of Sildenafil in Mouse, Rat, Dog, and Man," *Xenobiotica* 29(3): 297-310 (1999).

Compared to the 50 mg VIAGRA™ tablet, the sildenafil citrate lingual film demonstrated a 5-fold increase in systemic exposure at 30 minutes post-dosing. Moreover, the sildenafil citrate film showed a faster $T_{max}$ (30 minutes) as compared to the VIAGRA™ tablet (2 hours) and the oral solution (about 1 hour). The $C_{max}$ values for the 50 mg VIAGRA™ tablet and the sildenafil citrate lingual film were similar. Finally, the sildenafil citrate lingual film had a higher (1.2 times) overall systemic exposure ($AUC_{0-10hr}$) as compared to the 50 mg VIAGRA™ tablet.

Sildenafil citrate films as prepared above in Example 33 were tested for stability up to 3 months. The results of this testing are shown in Tables 17 and 18.

TABLE 17

Stability testing results for sildenafil citrate film.

| Storage Conditions | Sampling Time | Assay of API (% Label Claim) | Individual Unspecified RRT = 0.36 (%) | Total Degradation Products (%) |
|---|---|---|---|---|
| | | | Degradation Products | |
| Initial 25° C./60% RH | T = 0 | 104.3 | 0.45 | 0.45 |
| | 2 Weeks | 103.9 | 0.54 | 0.54 |
| | 4 Weeks | 105.9 | 0.39 | 0.39 |
| | 3 Months | 103.8 | 0.36 | 0.36 |
| 40° C./75% RH | 1 Week | 103.9 | 0.44 | 0.44 |
| | 2 Weeks | 105.0 | 0.58 | 0.58 |
| | 4 Weeks | 104.5 | 0.36 | 0.36 |
| | 3 Months | 105.6 | 0.36 | 0.36 |

TABLE 18

Stability testing results for sildenafil citrate film.

| Storage Conditions | Appearance* | PID† (sec) | Tensile Strength N/mm² | Average (n = 3) | Dissolution (Q = 80% @ 10 minutes) (min, max) |
|---|---|---|---|---|---|
| Initial 25° C./60% RH | Complies | 6 | 1.460 | 104 | (98, 110) |
| 2 Weeks | Complies | 6 | NT | 104 | (102, 105) |
| 3 Weeks | NT | NT | 1.196 | NT | NT |
| 4 Weeks | Complies | 6 | 2.431 | 107 | (103, 110) |
| 3 Months | Complies | 6 | 1.607 | 105 | (102, 109) |
| 40° C./75% RH | | | | | |
| 1 Week | Complies | 7 | 1.139 | 106 | (103, 109) |
| 2 Weeks | Complies | 6 | NT | 108 | (106, 109) |
| 3 Weeks | NT | NT | 5.363 | NT | NT |
| 4 Weeks | Complies | 6 | 2.657 | 104 | (103, 105) |
| 3 Months | Complies | 5 | 2.062 | 103 | (102, 103) |

*About 31 mm × 22 mm, Light blue opaque film
†Partial Immersion Dissolution Test
NT—Not tested The Unspecified Impurity (Table 17) detected was identified by spectral analysis to be a component of the cherry flavor used in the film. It is not a degradation product of the active (sildenafil citrate). Therefore, no degradation was detected greater than or equal to the limit of quantitation (0.1%). Accordingly, no degradation of active for this formulation was detected for up to 3 months at both 25° C. and 60% relative humidity and 40° C. and 75% relative humidity in real time data.

Figure 13:
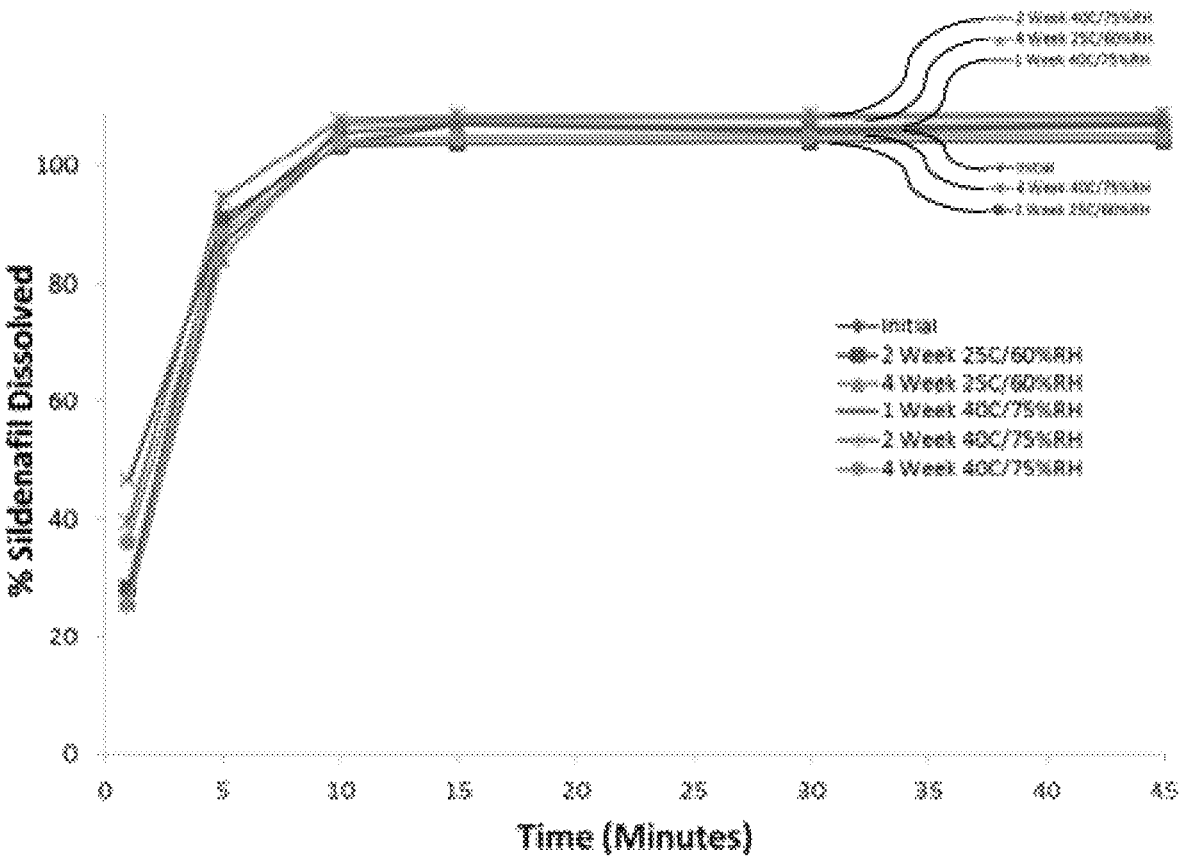
FIG. 13 shows the dissolution profile for sildenafil from sildenafil citrate films initially and stored for up to 4 weeks at 25° C. and 60% relative humidity or 40° C. and 75% relative humidity.

The assay results remained consistent which shows a mass balance. The dissolution results remained consistent which shows no slowing down of the dissolution rate. Overall, the data for this film supports a conclusion that the formulation (50 mg sildenafil based) is stable stability for up to 3 months at both 25° C. 60% relative humidity and 40° C. 75% relative humidity in terms of both assay/impurity level and dissolution. (See FIG. 13.)

Example 40: Pregabalin 150 mg

A film product of the invention was prepared as described above with the ingredients set forth in the table.

TABLE 19

Film product of the invention with 150 mg Pregabalin.

| Composition | Dry Basis (% w/w) | Dry Basis (mg/film) | Wet Basis (% w/w) | Weight Charged (g) |
|---|---|---|---|---|
| Pregabalin | 66.67 | 150.00 | 29.44 | 50.00 |
| pH Adjuster | 5.20 | 11.70 | 2.29 | 3.90 |
| Glycerin | 1.04 | 2.35 | 0.46 | 0.78 |
| Antifoaming Agent | 1.32 | 2.98 | 0.58 | 0,.99 |
| Starch Derivative | 0.67 | 1.50 | 0.29 | 0.50 |
| Artificial Sweetener | 0.73 | 1.65 | 0.32 | 0.55 |
| Monosaccharide Sweetener | 0.33 | 0.75 | 0.15 | 0.25 |
| Xylitol | 4.65 | 10.46 | 2.05 | 3.49 |
| Polyether | 1.00 | 2.25 | 0.44 | 0.75 |
| Flavoring Agent | 3.97 | 8.90 | 2.38 | 4.05 |
| Pullulan | 7.19 | 16.18 | 3.18 | 5.39 |
| Binder | 7.24 | 16.28 | 3.20 | 5.42 |
| Sum | 100.00 | 225.00 | 44.78 | 76.07 |
| Water Purified | | | 55.20 | 93.75 |
| Total | 100.00 | 225.00 | 100.00 | 169.83 |

Example 41: Tadalafil 5 mg, 10 mg, and 20 mg

A film products of the invention are prepared as described above with the ingredients set forth in the table.

TABLE 20

Film product of the invention with 5 mg, 10 mg, or 20 mg tadalafil.

| Composition | 5 mg film (% w/w) | 10 mg film (% w/w) | 20 mg film (% w/w) |
|---|---|---|---|
| Tadalafil | 6.02 | 11.35 | 20.38 |
| Monosaccharide Sweetener | 1.42 | 1.34 | 1.20 |
| Pullulan | 36.74 | 34.65 | 31.12 |
| Xylitol | 13.98 | 13.19 | 11.84 |
| Artificial Sweetener | 1.78 | 1.68 | 1.51 |
| Starch Derivative | 2.74 | 2.58 | 2.32 |
| Glycerin | 4.11 | 3.87 | 3.48 |
| Antifoaming agent | 4.11 | 3.87 | 3.48 |
| Opacifier | 5.82 | 5.49 | 4.93 |
| Polyether | 0.26 | 0.25 | 0.22 |
| Citric Acid | 12.31 | 11.61 | 10.43 |
| Colorant | 0.19 | 0.18 | 0.16 |
| Flavoring Agent | 10.53 | 9.94 | 8.92 |
| Sum | 100.00 | 100.00 | 100.00 |

Example 42: Content Uniformity of 100 ma Sildenafil Oral Soluble Films

2 Separate batches of films of the invention were prepared as described above with the ingredients set forth in Table 21 (Batch A) and Table 22 (Batch B) below:

Batch A:

TABLE 21

| | Film product of the invention with 100 mg Sildenafil base equivalent. | | |
|---|---|---|---|
| Component | Dry Basis (% w/w) | Dry Basis (mg/film) | Wet Basis (% w/w) |
| Sildenafil Citrate | 65.05 | 140.00 | 33.29 |
| Monosaccharide Sweetener | 0.54 | 1.16 | 0.28 |
| Pullulan | 12.77 | 27.47 | 6.53 |
| Xylitol | 5.31 | 11.43 | 2.72 |
| Artificial Sweetener | 0.67 | 1.45 | 0.35 |
| Starch Derivative | 1.04 | 2.23 | 0.53 |
| Glycerin | 1.55 | 3.35 | 0.80 |
| Antifoaming Agent | 1.55 | 3.35 | 0.80 |
| Opacifier | 0.78 | 1.67 | 0.40 |
| Polyether | 0.99 | 2.14 | 0.51 |
| Citric Acid | 0.05 | 0.11 | 0.03 |
| Colorant | 0.07 | 0.15 | 0.04 |
| Flavoring Agent | 5.96 | 12.83 | 3.05 |
| Carboxymethylcellulose | 2.98 | 6.41 | 1.52 |
| Sodium Chloride | 0.68 | 1.47 | 0.35 |
| Sum | 100 | 215.22 | 51.20 |
| Water Purified | | | 48.83 |
| Total | 100 | 215.22 | 100 |

Batch B:

TABLE 22

| | Film product of the invention with 100 mg Sildenafil base equivalent. | | |
|---|---|---|---|
| Component | Dry Basis (% w/w) | Dry Basis (mg/film) | Wet Basis (% w/w) |
| Sildenafil Citrate | 65.50 | 140.00 | 33.52 |
| Monosaccharide Sweetener | 0.54 | 1.16 | 0.28 |
| Pullulan | 15.76 | 33.69 | 8.07 |
| Xylitol | 5.35 | 11.43 | 2.74 |
| Artificial Sweetener | 0.68 | 1.45 | 0.35 |
| Starch Derivative | 1.05 | 2.23 | 0.53 |
| Glycerin | 1.57 | 3.35 | 0.80 |
| Antifoaming Agent | 1.57 | 3.35 | 0.80 |
| Opacifier | 0.78 | 1.67 | 0.40 |
| Polyether | 1.00 | 2.14 | 0.51 |
| Citric Acid | 0.05 | 0.11 | 0.03 |
| Colorant | 0.07 | 0.16 | 0.04 |
| Flavoring Agent | 6.00 | 12.83 | 3.07 |
| Carboxymethylcellulose | 0.09 | 0.19 | 0.05 |
| Sum | 100 | 213.76 | 51.17 |
| Water Purified | | | 48.83 |
| Total | 100 | 213.76 | 100 |

The films of Batch A had a moisture content of 3.94% wt and the films of Batch B had a moisture content of 3.93% wt based on the total weight of the film.

Ten individual unit doses were sampled from each of the 2 batches of the film. Each sampled individual unit dose had a desired amount (e.g., a dosage amount or label claim amount) of 140 mg of sildenafil citrate (equivalent to 100 mg of sildenafil base). The content of sildenafil in each sample was determined. The result for each of the sampled individual unit doses is reported below in Tables 23 and 24:

Batch A

TABLE 23

| Sample | % wt of Desired Amount |
|---|---|
| 1 | 100.9 |
| 2 | 96.1 |
| 3 | 92.5 |
| 4 | 97.1 |
| 5 | 98.4 |
| 6 | 97.2 |
| 7 | 99.1 |
| 8 | 97.2 |
| 9 | 97.1 |
| 10 | 100.0 |

Batch B

TABLE 24

| Sample | % wt of Desired Amount |
|---|---|
| 1 | 99.9 |
| 2 | 106.8 |
| 3 | 110.6 |
| 4 | 103.8 |
| 5 | 102.2 |
| 6 | 99.1 |
| 7 | 105.2 |
| 8 | 106.0 |
| 9 | 105.2 |
| 10 | 109.4 |

The appropriate statistical analysis was carried out for each batch and the results were as follows:

Batch A:
  Average % wt of Desired Amount=97.5%
  SD=2.3%
  RSD=2.4%
Batch B:
  Average % wt of Desired Amount=104.8%
  SD=2.3%
  RSD=2.4%

This content uniformity testing demonstrates that substantially equally sized individual dosage units of the films according to the invention contain an amount of active that varies by no more than 10% by weight from the desired amount, dosage amount, or drug label claim amount of the active.

While there have been described what are presently believed to be the certain desirable embodiments of the invention, those skilled in the art will realize that changes and modifications may be made thereto without departing from the spirit of the invention, and it is intended to include all such changes and modifications as fall within the true scope of the invention.

What is claimed is:

1. A cast film product comprising:
  a self-supporting film composition comprising a matrix from which self-supporting unit doses can be formed, said matrix comprising:
    (a) at least one linear polysaccharide film-forming polymer comprising pullulan in amounts of about 10% to about 35% by weight of the film composition;
    (b) an active present in amounts of about 6% to about 65% by weight of the film composition; and
    (c) a plasticizer composition present in an amount of about 10% to about 45% by weight based on the combined weight of the plasticizer composition and a total polymer content in the film product;

said plasticizer composition comprising xylitol and glycerin, wherein the glycerin is present in an amount that is equal to or less than the amount of the xylitol by weight;

and said matrix further comprising a resin;

wherein substantially uniformly sized unit doses of the film composition exhibit a disintegration value in the range of about 1 second to about 60 seconds as measured by suspending the unit dose film such that half of the unit dose film is submerged in water at 37° C. and determining the time for the submerged half of the unit dose film to separate from the suspended half.

2. The cast film product of claim 1, wherein the plasticizer composition further comprises a plasticizer selected from the group consisting of propylene glycol, triacetin and sorbitol.

3. The cast film product of claim 1, further comprising a sugar alcohol selected from the group consisting of sorbitol and maltitol.

4. The cast film product of claim 1, wherein the amount of the glycerin is equal to the amount of xylitol by weight.

5. The cast film product of claim 1, wherein the xylitol is present in an amount of about 10% to about 45% by weight based on the combined weight of the xylitol and the total polymer content.

6. The cast film product of claim 1, wherein the plasticizer composition is present in an amount of about 15% to about 22.5% by weight based on the combined weight of the plasticizer composition and the total polymer content.

7. The cast film product of claim 1, wherein the plasticizer composition is present in an amount of about 18% to about 21% by weight based on the combined weight of the plasticizer composition and the total polymer content.

8. The cast film product of claim 1, wherein the unit dose film has a thickness of from about 3 μm to about 500 μm.

9. The cast film product of claim 1, wherein the active is a neuromuscular drug.

10. The cast film product of claim 1, further comprising an additional polymer.

11. The cast film product of claim 10, wherein the additional polymer is selected from the group consisting of hydroxypropylmethyl cellulose, hydroxyethyl cellulose, hydroxypropyl cellulose, carboxymethyl cellulose, ethyl cellulose, hydroxypropyl ethyl cellulose, cellulose acetate phthalate, hydroxypropyl methyl cellulose phthalate, sodium alginate, polyethylene glycol, xanthan gum, tragancanth gum, guar gum, acacia gum, arabic gum, starch, gelatin, and combinations thereof.

12. The cast film product of claim 1, further comprising an acid.

13. The cast film product of claim 12, wherein the acid is selected from the group consisting of citric acid, formic acid, acetic acid, propionic acid, ascorbic acid, lactic acid, malic acid, tartaric acid, and combinations thereof.

14. The cast film product of claim 1, wherein the unit doses exhibit a disintegration value in the range of about 2 to about 10 seconds as measured by suspending the unit dose film such that half of the unit dose film is submerged in water at 37° C. and determining the time for the submerged half of the unit dose film to separate from the suspended half.

15. The cast film product of claim 1, wherein the film product has a tensile strength of about 0.8 N/mm$^2$.

16. The cast film product of claim 1, wherein the film product has a tensile strength of about 1 N/mm$^2$.

* * * * *